United States Patent
Shouldice

(10) Patent No.: US 11,980,484 B2
(45) Date of Patent: May 14, 2024

(54) SYSTEMS AND METHODS FOR MONITORING AND MANAGEMENT OF CHRONIC DISEASE

(71) Applicant: RESMED SENSOR TECHNOLOGIES LIMITED, Clonskeagh (IE)

(72) Inventor: Redmond Shouldice, Dublin (IE)

(73) Assignee: Resmed Sensor Technologies Limited, Dublin (IE)

(*) Notice: Subject to any disclaimer, the term of this patent is extended or adjusted under 35 U.S.C. 154(b) by 842 days.

(21) Appl. No.: 15/754,059

(22) PCT Filed: Aug. 26, 2016

(86) PCT No.: PCT/EP2016/070169
§ 371 (c)(1),
(2) Date: Feb. 21, 2018

(87) PCT Pub. No.: WO2017/032873
PCT Pub. Date: Mar. 2, 2017

(65) Prior Publication Data
US 2020/0297955 A1   Sep. 24, 2020

Related U.S. Application Data

(60) Provisional application No. 62/210,038, filed on Aug. 26, 2015.

(51) Int. Cl.
*A61B 5/02* (2006.01)
*A61B 5/00* (2006.01)
(Continued)

(52) U.S. Cl.
CPC ....... *A61B 5/7275* (2013.01); *A61M 16/0051* (2013.01); *A61M 16/026* (2017.08);
(Continued)

(58) Field of Classification Search
CPC ....... A61B 5/7275; A61B 5/01; A61B 5/0205; A61B 5/02416; A61B 5/0816;
(Continued)

(56) References Cited

U.S. PATENT DOCUMENTS

2007/0118054 A1   5/2007   Pinhas et al.
2010/0275921 A1   11/2010  Schindhelm et al.
(Continued)

FOREIGN PATENT DOCUMENTS

CN    103987314 A   8/2014
JP    H0880285 A    3/1996
(Continued)

OTHER PUBLICATIONS

A Yañez, D. Guerrero et al. "Monitoring breathing rate at home allows early identification of COPD exacerbations", Chest 142 1524-9, 2012 . GOLD criteria for COPD http://www.webmd.com/lung/copd/gold-criteria-for-copd.
(Continued)

*Primary Examiner* — Nader Bolourchi
(74) *Attorney, Agent, or Firm* — Botos Churchill IP Law LLP

(57) ABSTRACT

Systems and methods assist with managing a chronic disease of a user such as a chronic respiratory or cardiac disease. The system may include a physiological monitor adapted to be carried by the user and operative to sense a physiological parameter of the user by generating one or more signals. The system may include a management device operatively coupled with the physiological monitor to receive the signal(s) and derive the physiological parameter(s) of the user. The management device, such as with an included processor, may be configured to analyze the physiological and/or environmental parameters to detect a trigger pattern of the parameters, the trigger pattern indicative of a probable
(Continued)

event of exacerbation of the chronic respiratory and/or cardiac condition. The management device may then generate automated responses based on the trigger pattern such as by providing instructions for activities and/or treatment for the chronic condition.

49 Claims, 18 Drawing Sheets

(51) Int. Cl.

| | | |
|---|---|---|
| A61M 16/00 | (2006.01) | |
| A61M 16/06 | (2006.01) | |
| G01P 13/00 | (2006.01) | |
| G08B 21/04 | (2006.01) | |
| G16H 10/60 | (2018.01) | |
| G16H 20/00 | (2018.01) | |
| G16H 20/10 | (2018.01) | |
| G16H 20/13 | (2018.01) | |
| G16H 20/40 | (2018.01) | |
| G16H 40/63 | (2018.01) | |
| G16H 40/67 | (2018.01) | |
| G16H 50/20 | (2018.01) | |
| G16H 50/30 | (2018.01) | |
| G16H 50/50 | (2018.01) | |
| G16H 50/70 | (2018.01) | |
| A61B 5/01 | (2006.01) | |
| A61B 5/0205 | (2006.01) | |
| A61B 5/024 | (2006.01) | |
| A61B 5/0533 | (2021.01) | |
| A61B 5/08 | (2006.01) | |
| A61B 5/087 | (2006.01) | |
| A61B 5/11 | (2006.01) | |
| A61B 7/04 | (2006.01) | |
| A61M 15/00 | (2006.01) | |
| A61M 16/14 | (2006.01) | |
| G16H 20/30 | (2018.01) | |

(52) U.S. Cl.
CPC ............ *A61M 16/06* (2013.01); *G01P 13/00* (2013.01); *G08B 21/0453* (2013.01); *G16H 10/60* (2018.01); *G16H 20/00* (2018.01); *G16H 20/10* (2018.01); *G16H 20/13* (2018.01); *G16H 20/40* (2018.01); *G16H 40/63* (2018.01); *G16H 40/67* (2018.01); *G16H 50/20* (2018.01); *G16H 50/30* (2018.01); *G16H 50/50* (2018.01); *G16H 50/70* (2018.01); *A61B 5/01* (2013.01); *A61B 5/0205* (2013.01); *A61B 5/02416* (2013.01); *A61B 5/0533* (2013.01); *A61B 5/0816* (2013.01); *A61B 5/082* (2013.01); *A61B 5/087* (2013.01); *A61B 5/1102* (2013.01); *A61B 7/04* (2013.01); *A61M 15/009* (2013.01); *A61M 16/14* (2013.01); *A61M 2202/0208* (2013.01); *A61M 2205/18* (2013.01); *A61M 2205/3553* (2013.01); *A61M 2205/3561* (2013.01); *A61M 2205/3584* (2013.01); *A61M 2205/42* (2013.01); *A61M 2205/502* (2013.01); *A61M 2205/52* (2013.01); *A61M 2205/581* (2013.01); *A61M 2205/583* (2013.01); *A61M 2230/06* (2013.01); *A61M 2230/42* (2013.01); *A61M 2230/50* (2013.01); *A61M 2230/63* (2013.01); *G16H 20/30* (2018.01)

(58) Field of Classification Search
CPC ....... A61B 5/082; A61B 5/087; A61B 5/1102; A61B 7/04; A61B 5/0073; A61B 5/08; A61B 2560/0242; A61B 5/746; A61B 5/0533; A61M 16/0051; A61M 16/026; A61M 16/06; A61M 16/14; A61M 2202/0208; A61M 2205/18; A61M 2205/3553; A61M 2205/3561; A61M 2205/3584; A61M 2205/42; A61M 2205/502; A61M 2205/52; A61M 2205/581; A61M 2205/583; A61M 2230/06; A61M 2230/42; A61M 2230/50; A61M 2230/63; A61M 2230/65; A61M 15/00; A61M 2205/3592; A61M 2230/60; G01P 13/00; G08B 21/0453; G16H 10/60; G16H 20/00; G16H 20/10; G16H 20/13; G16H 20/40; G16H 40/63; G16H 40/67; G16H 50/20; G16H 50/30; G16H 50/50; G16H 50/70; G16H 20/30
See application file for complete search history.

(56) References Cited

U.S. PATENT DOCUMENTS

| | | |
|---|---|---|
| 2011/0245633 A1 | 10/2011 | Goldberg et al. |
| 2012/0041279 A1 | 2/2012 | Freeman et al. |
| 2012/0238834 A1 | 9/2012 | Hornick |
| 2013/0066395 A1 | 3/2013 | Simon et al. |
| 2014/0024917 A1* | 1/2014 | McMahon ............... G01S 13/18 600/407 |
| 2014/0088373 A1* | 3/2014 | Phillips ................ A61B 5/0507 600/301 |
| 2015/0094544 A1 | 4/2015 | Spolin et al. |
| 2015/0157794 A1 | 6/2015 | Roy et al. |
| 2015/0164375 A1 | 6/2015 | Schindhelm et al. |
| 2015/0216424 A1 | 8/2015 | McMahon et al. |
| 2016/0287122 A1 | 10/2016 | Heneghan |

FOREIGN PATENT DOCUMENTS

| | | |
|---|---|---|
| JP | 2004000555 A | 1/2004 |
| JP | 2006520659 A | 9/2006 |
| JP | 2008090824 A | 4/2008 |
| JP | 2008246176 A | 10/2008 |
| JP | 2009532072 A | 9/2009 |
| JP | 2011104102 A | 6/2011 |
| JP | 2011104104 A | 6/2011 |
| JP | 2012507309 A | 3/2012 |
| JP | 2014530670 A | 11/2014 |
| WO | 2004084116 A1 | 9/2004 |
| WO | 2007052108 A2 | 5/2007 |
| WO | 2007143535 A2 | 12/2007 |
| WO | 2008057883 A2 | 5/2008 |
| WO | 2010009382 A2 | 1/2010 |
| WO | 2010036700 A1 | 4/2010 |
| WO | 2010091168 A1 | 8/2010 |
| WO | 2011006199 A1 | 1/2011 |
| WO | 2011109716 A2 | 9/2011 |
| WO | 2013043847 A1 | 3/2013 |
| WO | 2013177621 A1 | 12/2013 |
| WO | 2014015238 A1 | 1/2014 |
| WO | 2015006364 A2 | 1/2015 |
| WO | 2015054134 A1 | 4/2015 |
| WO | 2015065674 A1 | 5/2015 |
| WO | 2015179911 A1 | 12/2015 |
| WO | 2016074042 A1 | 5/2016 |
| WO | 201729284 A1 | 2/2017 |
| WO | 2017029317 A1 | 2/2017 |
| WO | 2014047310 A1 | 3/2017 |

OTHER PUBLICATIONS

B.B. Shu, M. O'Brien, C. Blake, R. Shouldice, C. Hanley, T.J. McDonnell and S.C. Donnelly, "Telemedicine: Remote Clinical Monitoring in COPD—A Pilot Study", Irish Thoracic Society Annual Scientific Meeting, (vol. 34, p. 450), Nov. 2008.

(56) References Cited

OTHER PUBLICATIONS

Bartels MN, Jelic S, Ngai P, Basner RC, DeMeersman RE., "High-frequency modulation of heart rate variability during exercise in patients with COPD". Chest. Sep.; 124(3):863-9, 2003.
C Camillo et al. "Improvement of heart rate variability after exercise training and its predictors in COPD" Respiratory Medicine, vol. 105, Issue 7, 1054-1062, 2011.
C. Heneghan, C. P. Chua, J. Garvey, P. de Chazal, R. Shouldice, P. Boyle, W. McNicholas. A Portable Automated Assessment Tool for Sleep Apnea Using a Combined Holter-Oximeter. Journal SLEEP, Oct. 2008.
CA Lewis, W Fergusson, T Eaton, I Zeng, J Kolbe, "Isolated nocturnal desaturation in COPD: prevalence and impact on quality of life and sleep", Thorax, 2009.
CP van Schayck, NH Chavannes. "Detection of asthma and chronic obstructive pulmonary disease in primary care". Eur Respir J Suppl. Jan.;39:16s-22s, 2003.
Koskela HO, Koskela AK, Tuklaineu HO."Bronchoconstriction due to cold weather in COPD. The roles of direct airway effects and cutaneous reflex mechanisms." Chest. Sep;110(3):632-6, 1996.
MA Cretikos, R Bellomo, K Hillman, J Chen, S Finfer and A Flabouris. "Respiratory rate: the neglected vital sign" MJA; 188 (11): 657-659. 2008.
McSharry DG, Ryan S, Calverley P, Edwards JC, MoNicholas WT. "Sleep quality in chronic obstructive pulmonary disease." Respirology. Oct.;17(7):1119-24, 2012.
Mordechai Yigla, Naveh Tov, Anna Solomonov, Ami-Hai E. Rubin, Dan Harlev, "Difficult-to-Control Asthma and Obstructive Sleep Apnea" Journal of Asthma, vol. 40, No. 8 : pp. 865-871, 2003.
Notification of International Preliminary Report on Patentability issued in corresponding PCT application No. PCT/EP2016/070169 dated Mar. 8, 2018.
Pitta F et al: "Characteristics of physical activities in daily life in chronic obstructive pulmonary disease." Am J Respir Crit Care Med; 171(9): 972-7, 2005. The role of physical activity in COPD patients: http://universimed.com/node/100502.
R Shouldice, C Heneghan, G Petres, A Zaffaroni, P Boyle, W McNicholas, P de Chazal, "Real time breathing rate estimation from a non contact biosensor", IEEE EMBC, 2010, pp. 630-633, Aug. 31-Sep. 4, 2010.
T Ballal, R Shouldice, C Heneghan, A Zhu, "Breathing rate estimation from a non-contact biosensor using an adaptive IR notch filter" IEEE Topical Conference on Biomedical Wireless Technologies, Networks, and Sensing Systems (BioWireleSS), 5-8, 2012.
T. Ballal, et al., "A pilot study of the nocturnal respiration rates in COPD patients in the home environment using a non-contact biomotion sensor". Physiol Meas. Dec. 2014;35(12):2513-27.
PCT/EP2016/070169 International Search Report, dated Mar. 15, 2017.
Office Action for Japanese Patent Application No. 2018-510768 dated Aug. 18, 2020.
The Second Office Action for Chinese Patent Application No. 201680057881.8, dated May 7, 2021.
Office Action for corresponding JP Application No. P2021-114442 dated Jul. 12, 2022 with English Translation (12 pages).

* cited by examiner

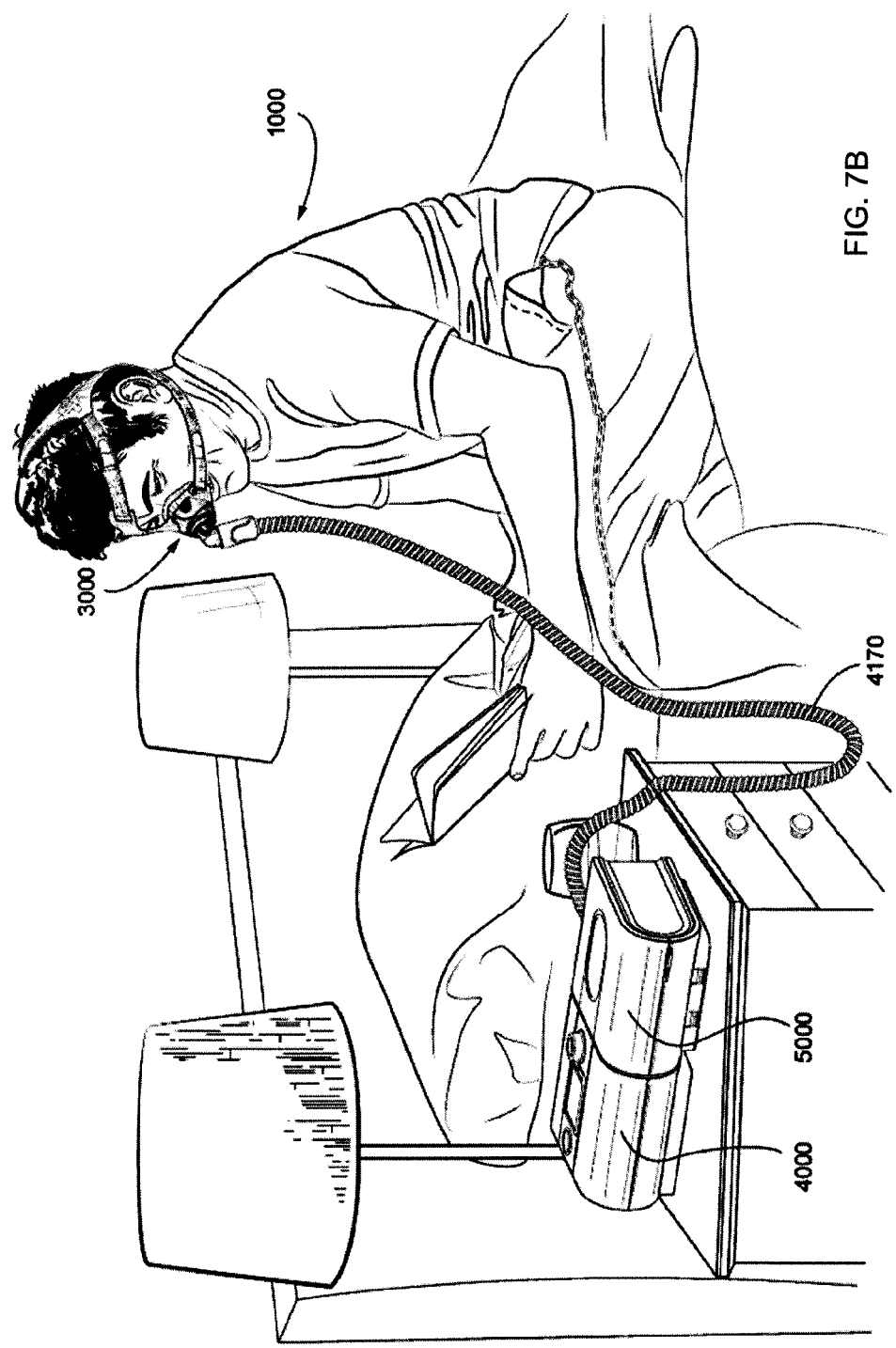

SYSTEMS AND METHODS FOR MONITORING AND MANAGEMENT OF CHRONIC DISEASE

CROSS-REFERENCE TO RELATED APPLICATIONS

The present application is a national phase entry under 35 U.S.C. § 371 of International Application No. PCT/EP2016/070169 filed Aug. 26, 2016, published in English, which claims priority from U.S. Provisional Patent Application No. 62/210,038 filed Aug. 26, 2015, all of which are incorporated herein by reference.

BACKGROUND OF THE TECHNOLOGY

Field of the Technology

The present technology relates to systems and methods for monitoring a patient suffering from a chronic disease, such as a chronic respiratory and/or cardiac disease, including, for example, asthma, chronic obstructive pulmonary disease (COPD) or congestive heart failure (CHF), based on multiple sources of information, and managing the patient's condition in the context of their overall lifestyle.

Description of the Related Art

Asthma and COPD

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterized by particular events, e.g., apneas, hypopneas, and hyperpneas.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking, occupational exposures, air pollution and genetic factors. Symptoms include dyspnea on exertion, elevated breathing rates (tachypnea), chronic cough and sputum production.

Heart failure is a chronic condition. The severity of the disease can be classified using New York Heart Association (NYHA) subjective and objective categories (reproduced in the tables below). Heart failure can also be considered in classes such as systolic and diastolic heart failure. Heart failure can be relatively stable over long periods of time, with reduced cardiovascular function, with events of an acute nature. In such acute phases, the patient may experience worsening of symptoms such as dyspnea (difficulty breathing), gallop rhythms, increased jugular venous pressure, orthopnea, and can include overt congestion (build-up of fluid in the pulmonary cavity). Such excess fluid may lead to weight gain of several kilograms. However, by the time overt congestion has occurred, there are limited options for the doctor to help restabilize the patients, and in many cases the patient requires hospitalization. Therefore, means of detecting the events early, and providing overall management of the chronic condition, are highly desirable.

| CLASS | PATIENT SYMPTOMS |
| --- | --- |
| I | No limitation of physical activity. Ordinary physical activity does not cause undue fatigue, palpitation, dyspnea (shortness of breath). |
| II | Slight limitation of physical activity. Comfortable at rest. Ordinary physical activity results in fatigue, palpitation, dyspnea (shortness of breath). |
| III | Marked limitation of physical activity. Comfortable at rest. Less than ordinary activity causes fatigue, palpitation, or dyspnea. |
| IV | Unable to carry on any physical activity without discomfort. Symptoms of heart failure at rest. If any physical activity is undertaken, discomfort increases. |

| CLASS | OBJECTIVE ASSESSMENT |
| --- | --- |
| A | No objective evidence of cardiovascular disease. No symptoms and no limitation in ordinary physical activity. |
| B | Objective evidence of minimal cardiovascular disease. Mild symptoms and slight limitation during ordinary activity. Comfortable at rest. |
| C | Objective evidence of moderately severe cardiovascular disease. Marked limitation in activity due to symptoms, even during less-than-ordinary activity. Comfortable only at rest. |
| D | Objective evidence of severe cardiovascular disease. Severe limitations. Experiences symptoms even while at rest. |

As with heart failure, there can be acute exacerbations of COPD, often due to bacterial or viral infections. Untreated flu or the common cold (especially with associated wheezing and coughing) can lead to life threatening pneumonia. Many of the symptoms of asthma are common to COPD—and especially triggers such as air pollution, strong scents/fumes, smoke, cold dry air, and hot air (i.e., extremes in temperature).

Asthma is a lung disorder whereby there is chronic inflation in the tubes that carry air to the lungs. It can be intermittent and a person may go for weeks or even months with no apparent symptoms. Traditionally, a person will learn to recognize their own symptoms and triggers (often with limited success). Additionally, a person with asthma may not realize that they are at elevated risk of COPD (e.g., smokers). For asthma and COPD, the disease progression can be gradual as the user adapts to the worsening condition. Thus, diagnosis can unfortunately be delayed.

Generally speaking, asthma is most common in childhood, with COPD more usually seen in adults (and especially in older adults that smoke).

Additionally, these conditions may be worsened where a person has a high BMI (body mass index); i.e., is obese. Such subjects with asthma or COPD may also have Obesity Hypoventilation Syndrome (OHS), exemplified by daytime changes in respiration related to hypercapnia (abnormally elevated carbon dioxide ($CO2$) levels in the blood).

Where COPD and OSA (Obstructive Sleep Apnea) are present at the same time (overlap syndrome), there can be a substantially greater risk of morbidity and mortality.

Environmental Triggers and Other Symptoms

Asthma and COPD sufferers have risk factors related to weather conditions, activity levels, prior trends of exacerbation, and a variety of physiological parameters, including heart rate, galvanic skin response and respiration. Further, it is noted that asthma and particularly COPD sufferers are sensitive to environmental pollution, and to elevated ozone levels.

Allergies such as hay fever (Allergic Rhinitis) may worsen existing asthma (e.g., reactions to allergens such as pollen, mold, dust, or animal dander). Sufferers may also experience skin issues such as eczema.

Persons may also experience exercise related triggers (e.g., an asthma attack during or after exercise), and exhibit increasing breathlessness and respiratory distress as their COPD condition worsens.

A person may also experience mucus of varying color and volume. An asthmatic cough may be productive (producing phlegm) or non-productive (dry cough), and may or may not be accompanied by wheezing (a high pitched whistling sound resulting from the constricted airways). Wheezing and crackling may be inspected by a physician using auscultation for example.

Other conditions such as heart disease (e.g., congestive heart failure) should be considered in the context of a person with COPD (in terms of (a) when both diseases are present, and/or (b) in the ability to share many aspects of a monitoring and management system as both diseases exhibit symptoms of shortness of breath with exertion—albeit for different reasons).

Classification Based on Quality of Life and Symptoms

Asthma

Asthma may be classified into three categories related to severity:

Baseline state: Subjective quality of life good or excellent, with no coughing or wheezing, good or great sleep, peak flow via spirometer within an arbitrary threshold (e.g., 20%) of healthy personal baseline. May be taking medication to control asthma.

Worsening state: Quality of life partially impaired, breathing showing some impairment (some shortness of breath or feeling of chest tightness), sleep quality degraded, peak flow may drop as low as 50% of the expected baseline. Will be taking medication and increasing dose, with possibility of specific inhaler use as symptoms worsen.

Pre-exacerbation Exacerbation state: Feeling very unwell, with severe breathing changes (extended shortness of breath, elevated rate), and impact on day to day activities. Taking medication including rescue inhaler as condition worsens. Risk of asthma attack, and likely to seek/require medical help.

COPD

The Global Initiative for Chronic Obstructive Lung Disease (GOLD) classification of COPD classifies a person based on airflow limitation into four stages. The key parameters are forced expiratory volume (FEV1) per second, and forced vital capacity (FVC) (total exhaled breath) whereby both may be measured in liters. For people with normal lung function, FEV1 is at least 70% of FVC.

|  | FEV1/FVC | FEV1 |
| --- | --- | --- |
| Stage I: Mild COPD | FEV1/FVC <0.70 | FEV1 ≥80% normal |
| Stage II: Moderate COPD | FEV1/FVC <0.70 | FEV1 50-79% normal |
| Stage III: Severe COPD | FEV1/FVC <0.70 | FEV1 30-49% normal |
| Stage IV: Very Severe COPD | FEV1/FVC <0.70 | FEV1 <30% of normal, or <50% of normal with chronic respiratory failure present |

Treatment Systems

A range of therapies have been used to treat or ameliorate the conditions brought on by asthma and COPD. Furthermore, otherwise healthy individuals may take advantage of such therapies to prevent these disorders from arising or worsening.

A sufferer may take an oral systemic steroid or use inhaled steroids. Such systemic treatment can be used to treat asthma attacks, and to help achieve better control of asthma. It is suggested that the introduction of anti-inflammatory inhalers early in the progression of the disease can be helpful; therefore, early screening and diagnosis is desirable. Daily medication might involve corticosteroids in order to reduce inflammation in the lungs, and thus reduce sensitivity to airborne irritants.

Anti-inflammatory asthma inhalers deliver medication directly to the lungs. For serious exacerbations, rapid relief may be delivered by short acting medication such as beta-antagonists, in order to help relax tightened muscles, and aid air flow to the lungs.

Bronchodilators (either quick or slow onset) may also be used in the case of COPD, in addition to corticosteroids, antibiotics, and supplemental oxygen; chronic bronchitis is related to airways filled with mucus and being swollen, whereas with emphysema the alveoli are compromised.

Monitoring Systems

For patients suffering from asthma or COPD (or indeed congestive heart failure—CHF), it is a goal to prevent readmission of those patients to a hospital due to exacerbations. For example, COPD subjects typically experience periods of relative stability punctuated by acute exacerbations, triggered by opportunistic infections, and regularly result in significant unscheduled medical intervention, which impose both a significant cost burden on the healthcare system and quality-of-life impact on the sufferer and their family. Exacerbations are frequently under-reported—it is estimated that perhaps less than 50% are reported by patients.

However, because exacerbation may occur at any given time, not just while a patient is home or in bed, it is desirable to be able to monitor and assess the health of the patient at all or at least most times, including while the patient is away from home or otherwise on the move. Accordingly, it may be very helpful to have a portable and regular way of measuring FEV, and other parameters of the patient's health.

There are "mHealth" monitoring solutions on the market that monitor physiological parameters remotely. These may include triggers based on single or multiple parameters.

U.S. Publication No. 2007/0118054 discloses a system for monitoring vital signs for the prediction and treatment of physiological ailments.

U.S. Publication No. 2010/0275921 discloses a system for detecting a severity change in respiratory insufficiency (RI) or COPD of a patient.

U.S. Publication No. 2015/0164375 discloses a cardiopulmonary health monitoring apparatus that extracts one or more sleep disordered breathing features based on bodily movement of a patient during a monitoring session, and predicting whether a clinical event is likely to occur based on the extracted features.

International Patent Application Publication No. WO/2010/091168 describes an apparatus, system, and method for monitoring a person suffering from a chronic medical condition predicts and assesses physiological changes which could affect the care of that subject.

Therapies

A range of therapies have been used to treat or ameliorate respiratory conditions. Furthermore, otherwise healthy individuals may take advantage of such therapies to prevent respiratory disorders from arising.

Nasal Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion by pushing the soft palate and tongue forward and away from the posterior oropharyngeal wall.

Non-invasive ventilation (NIV) therapy provides ventilatory support to a patient through the upper airways to assist the patient in taking a full breath and/or maintaining adequate oxygen levels in the body by doing some or all of the work of breathing. NIV is provided via a non-invasive patient interface. NIV has been used to treat CSR, OHS, COPD, NMD, and Chest Wall disorders.

Diagnosis and Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g., with a face region of the patient, to facilitate the delivery of gas at a pressure at sufficient variance with ambient pressure to effect therapy, e.g., a positive pressure of about 10 cmH$_2$O. For other forms of therapy, such as the delivery of oxygen, the patient interface may not include a seal sufficient to facilitate delivery to the airways of a supply of air at a positive pressure of about 10 cmH$_2$O.

Respiratory Pressure Therapy (RPT) Devices

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

One known RPT device used for treating sleep disordered breathing is the S9 Sleep Therapy System, manufactured by ResMed, which proves CPAP therapy. Another example of an RPT device is a ventilator. Ventilators such as the ResMed Stellar™ Series of Adult and Paediatric Ventilators may provide invasive and non-invasive non-dependent ventilation therapy for a range of patients for treating a number of conditions such as but not limited to NMD, OHS and COPD.

RPT devices typically comprise a pressure generator, such as a motor-driven blower or a compressed gas reservoir, and are configured to supply pressurised air to the airways of a patient. The outlet of the RPT device is connected via an air circuit to a patient interface such as those described above.

There may still be a need for a system that can not only monitor the health of the user, but can also help those users understand how to improve their own quality of life, such as by understanding their symptoms and triggers, and how they respond to medication.

Additionally, it is desirable for the system to have access to, and be capable of processing, as much data relevant to the user's condition as possible. In this respect, it is also desirable that the system be capable of monitoring the patient for as much of the day and night as possible, not just when the patient is in bed.

BRIEF SUMMARY OF THE TECHNOLOGY

The present technology is directed towards providing medical and/or lifestyle devices used in the diagnosis, amelioration, treatment, or prevention of respiratory disorders having one or more of improved comfort, cost, efficacy, ease of use and manufacturability.

Some versions of the technology may include a lifestyle management system for managing a chronic respiratory and/or cardiac condition of a user. The system may include a management device, including a processor. The device may be configured for communication with a physiological monitor to receive a sensed physiological parameter of the user. The physiological monitor may be adapted to be carried by the user and operative to sense the physiological parameter of the user. One or more processors of the management device may be configured to access a plurality of physiological and environmental parameters. The plurality of physiological and environmental parameters may include the sensed physiological parameter. The one or more processors of the management device may be configured to analyze the plurality of physiological and environmental parameters to detect a trigger pattern of the parameters. The trigger pattern may be indicative of a probable event of exacerbation of the chronic respiratory and/or cardiac condition. The one or more processors of the management device may be configured to control activation of an automated response based on the detection of the trigger pattern indicative of a probable event of exacerbation of the chronic respiratory and/or cardiac condition.

Some versions of the present technology may include a lifestyle management method for managing a chronic respiratory and/or cardiac condition of a user. The method may be implemented in a management device, including a processor, such that the device may be configured for communication with a physiological monitor, and the physiological monitor may be adapted to be carried by the user and operative to sense a physiological parameter of the user. The method may involve receiving the sensed physiological parameter of the user. The method may involve accessing a plurality of physiological and environmental parameters. The plurality of physiological and environmental parameters may include the sensed physiological parameter. The method may involve analyzing the plurality of physiological and environmental parameters to detect a trigger pattern of the parameters. The trigger pattern may be indicative of a probable event of exacerbation of the chronic respiratory and/or cardiac condition. The method may include controlling activation of an automated response based on the detection of the trigger pattern indicative of a probable event of exacerbation of the chronic respiratory and/or cardiac condition.

Some versions of the present technology may include a computer-readable memory storage medium having program instructions encoded thereon configured to cause a processor to perform a lifestyle management method for managing a chronic respiratory condition of a user, the method including any one of the methods described herein.

In some versions, the physiological monitor may be one of a ballistocardiogram sensor, a heart rate monitor, a photoplethysmography sensor, a galvanic skin response sensor, and a temperature sensor. Optionally, a parameter of the plurality of physiological and environmental parameters may be sensed by non-contact radio frequency motion sensor. The plurality of physiological parameters may include detected physiological parameters from sensors in different locations. The sensors of different locations may include a bedroom sensor and a non-bedroom sensor. The management device may be portable and integrated with a portable alarm triggered by the automated response. The trigger pattern indicative of a probable event of exacerbation of the chronic respiratory condition may be indicative of one of an asthma condition and a COPD condition. The management device may be further configured to track a baseline threshold of the sensed physiological parameter. The system may include processor control instructions for the processor for analyzing the plurality of physiological and environmental parameters that include rule thresholds that are varied based on adaptive probabilistic weightings from one or both of user specific and population based demographic data.

In some versions, the sensed physiological parameter is one of breathing, heart rate, blood pressure, and electrodermal response. The sensed physiological parameter may be tracked during daytime and nighttime by the management device. The tracked physiological parameter may be an audio parameter produced by the user during sleep. Optionally, the plurality of physiological and environmental parameters may include an environmental parameter based on at least one of climate data and geographic data.

The management device may be configured to interface with a medical information system storing medical records of the user, wherein the analysis of the plurality of physiological and environmental parameters to detect a trigger pattern of the parameters may include an analysis of a parameter based on data accessed from the medical records of the user. The automated response based on the detection of the trigger pattern may include a communication for application of a treatment by a treatment device adapted for treating the chronic respiratory condition of the user. The automated response based on the detection of the trigger pattern may include a communication for warning a user to refrain from a predetermined activity. The automated response based on the detection of the trigger pattern may include a communication for instructing a user to effect a treatment of the chronic respiratory condition before performing a predetermined activity.

In some versions, the management device may include a smart-phone or smart-watch. The system may include the physiological monitor. The system may include a smart-case, and the management device may be configured to detect a proximity of the smart-case. The smart-case may house the physiological monitor. The smart-case may house a treatment device. The processor of the management device may be configured to determine a treatment dosage based on the trigger pattern. In some cases, the automated response may include a communication for managing the determined treatment dosage. In some cases, such as when the chronic respiratory condition managed is asthma, the determined treatment dosage may be one or more of: a number of puffs from an inhaler; and a quantity on a metered inhaler. In some cases, such as when the chronic respiratory condition is COPD, the determined treatment dosage may be a treatment from one or more of an inhaler, nebulizer, and supplemental oxygen tank. In terms of a portable case (smart case) optionally containing one or more cartridges of medication, contactless sensing can be performed from the case using active RF methods (e.g., an RF chip module), or via the phone's inbuilt sensors/transducers; e.g., heart rate measurement using an optical sensor, sonar using the phone's loudspeaker and microphone, a custom microphone/speaker assembly in the smart case, etc. The case may also contain a spirometer, and other gas sensing apparatus.

Optionally, the management device may include an input interface for receiving parameters of the plurality of physiological and environmental parameters. The parameters may include any one or more of exercise data, breathing data, a cardiac data, a skin temperature data, skin coloration data, a sleep quality data, and blood pressure data, locally airborne irritant data, locally seasonal factor data, local weather data, and an indoor environmental data.

Some versions of the present technology may include an apparatus for managing a chronic respiratory and/or cardiac condition of a user. The apparatus may include a portable housing adapted for being carried or worn by the user. The apparatus may include a sensor configured to derive at least one parameter from a physiological characteristic of the user. The apparatus may include a processor for predicting a status of the chronic respiratory and/or cardiac condition based on at the at least one derived parameter. The apparatus may include a user interface for alerting the user concerning the chronic respiratory and/or cardiac condition based on the predicted status of the chronic respiratory condition. In some cases, each of the processor and user interface may be integrated within the portable housing of the apparatus. The apparatus may be a smartphone, such as a mobile phone with a programmable processor. The apparatus may be a smartwatch. Optionally, the processor may be configured to determine whether a portable treatment device of the user is within range of the apparatus. The processor may be configured to generate an alert based on the determination, such as when the portable treatment device is or is not within range of the apparatus. The sensor may be integrated into the housing of the apparatus.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:

FIG. 7B shows an RPT device 4000 in use on a patient 1000 with a nasal mask 3000.

In FIG. 9D, arrows with solid lines indicate an actual flow of information, for example via an electronic signal.

DETAILED DESCRIPTION OF EXAMPLES OF THE TECHNOLOGY

Figure 1:
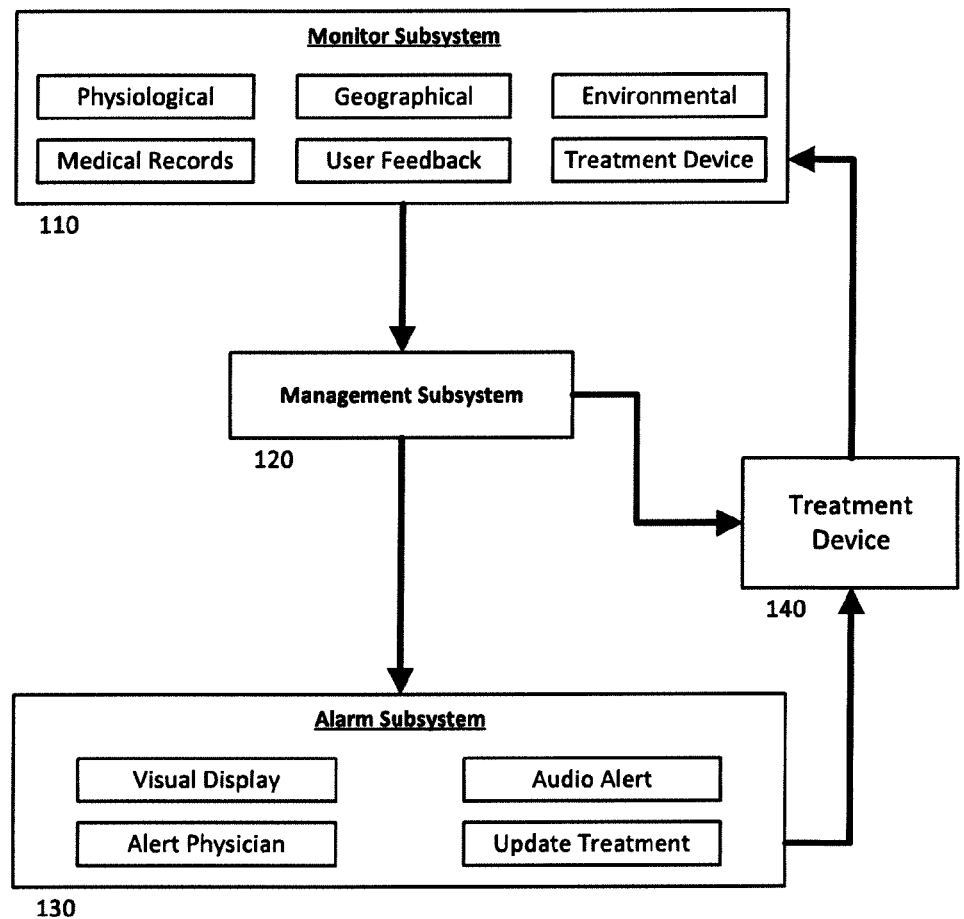
FIG. 1 shows a system including a patient monitor, a management device connected to the monitor and programmed to manage a chronic disease of the patient based on inputs from the patient monitor, an alarm connected to the management device and programmed to alert the patient based on outputs from the management device, and a treatment device for treating the patient's chronic disease, in accordance with an embodiment of the present disclosure.

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

System Architecture

Examples of the systems outlined herein may be configured to monitor and/or detect user specific patterns related to onset and severity of chronic respiratory diseases, as well as to treatment and prevention of the monitored chronic diseases (e.g., a medication alert, titration, or exacerbation prevention system). The system may rely on the analysis of a combination of both physiological and environmental parameters, as well as other factors. Thus, the system may include one or more computing devices, such as one or more servers, with one or more processor(s) programmed or configured to perform the described functionalities of each of the subsystem(s).

As a whole, the system may be configured to evaluate, on a holistic basis, the monitored chronic disease (or monitored pre-chronic disease), and may aggregate multiple sensor, lifestyle and environmental parameters in order to deliver tangible health improvements.

At a high level, the system may implement methodologies, such as with software algorithms, for reading data from a multitude of sensors and services, processing the data, and adapting system parameters based on the data as well as based on previously collected datasets. Some or all of the sensors may gather physiological data readings from a user of the system. The system can also intervene to adjust medication levels, interact with a physician, and interact with the user in a manner intended to predict, prevent or reduce the severity of an exacerbation or worsening of the condition being monitored. In some cases, the system may include any of the components, devices and/or methodologies of the apparatus, system and method for chronic disease monitoring described in International Patent Application Publication Nos. WO 2007/143535, WO 2008/057883, WO 2010/036700, WO 2010/091168, WO 2014/015238 and WO 2015/179911, and U.S. Provisional Application Ser. No. 62/205,129, the entire disclosures of which are incorporated herein by reference.

A user might, for example, have been diagnosed with SDB (sleep disordered breathing), and be using a therapy device (e.g., PAP or RPT device). The system may be programmed to learn the user's behaviors, triggers and symptoms, e.g., use current and previous parameters (prior knowledge) of the user and environmental cues to prompt action such as flagging an alert or delivering therapy. For example, the system may be configured to detect an elevated breathing rate, or progression from deeper to shallower breathing patterns (indicative of breathlessness as might be reported by the person), or periodic (such as Cheyne Stokes Respiration) patterns in the breathing waveform over time. Additionally, the system may be configured to detect coughing during the day or at night (e.g., in REM sleep later in the night versus in deep sleep, and the impact on sleep architecture; as an aside, sneezing would not be expected in REM sleep due to REM atonia), and particular patterns of wheezing, particularly during expiration. During non REM sleep, the basal metabolic rate and ventilator drive decreases. For example, the system may be configured to determine sleep scores based on such factors as quality and duration of sleep, and evaluate the user's coughing based on the sleep score, since sleep scores tend to decrease due to coughing (especially where there are frequent coughing fits). Acoustic analysis can also be applied to estimate the cough frequency, severity, and classify the type of cough. Such sleep score or sleep stage determinations may be implemented with any suitable methodology, including, for example, the methodologies disclosed in International Patent Application No. PCT/US2014/045814, filed on Jul. 8, 2014, the entire disclosure of which is incorporated herein by reference.

An increase in insomnia may be seen as chronic diseases such as COPD worsen. Interventions to improve sleep quality (such as driving sleep hygiene improvements using cognitive behavioural therapy CBT or prescription or non-prescription sleeping pills) may be helpful; objective improvements in sleep quality can then be measured over time—e.g., using sleep parameter estimation from non-contact biomotion sensor signal processing.

Similar determinations may be made during daytime, during which coughing may result in experience of subjective and/or objective measures of fatigue and lethargy (often in combination with a seasonal allergy to pollen).

One example realization of the system is targeted at helping people with known asthma or COPD, specifically by proactively advising them of their risk level prior to exacerbation, and utilizing user input in order to refine future detection and future advice. Similarly, the system may be designed to screen for possible asthma or possible COPD, e.g., to help people that have not yet identified the cause of certain symptoms, and prompt them to visit their physician. For the case of CHF, a person may be stable, but then develop an infection of the lungs known as pneumonia or other respiratory infections. Similarly, a person with advanced COPD is at increased risk of such life threatening exacerbations, and cycles of COPD and pneumonia can lead to potential respiratory failure. Fatigue (especially ongoing or chronic fatigue) is a sign of pneumonia; other indicators of pneumonia are a shortness of breath (including a difficulty in "catching a breath"), increase in temperature (fever), "chills", congestion, and productive coughs (such as green mucus). Chronic and acute fatigue estimation/detection can be achieved by the processing of current and historical sleep parameters, and/or via reaction times derived from the use of applications such social medial, messaging, and games on portable devices such as smart phones. For example, the system may implement any of the detection methodologies, including for example, subjective and/or objective measures of fatigue such as a predictor of congestion, exacerbation and/or pneumonia, described in International Patent Application Publication No. WO/2015/054134, the entire disclosure of which is incorporated herein by reference.

Additionally, the system may be configured to ensure that a user is reminded to keep their inhaler/medication in close proximity, may also be configured to communicate with a medical professional, and may further be configured to automatically instruct, adjust and/or deliver medication to the user (e.g., without direct assistance from a medical professional). For example, a treatment for an infection such as *Streptococcus pneumoniae* or bacterial influenza (e.g., related to pneumonia), or a diuretic to help rid the body of excess fluid and sodium (e.g., related to CHF).

FIG. 1 depicts a high-level functional block diagram of a system 100 in in some versions of the present technology. The system 100 may include a monitor subsystem 110 for monitoring the user, such as by gathering data about the user and/or the user's environment. The gathered data may include any one or combination of physiological data, geographical data, environmental data, medical records, user feedback, and other data from a treatment device 140 of the user, as well as forms of data useful for monitoring the user's condition. The data may be retrieved by accessing other systems/devices designed for monitoring such information, received from suitable sensor(s), or input in response to prompts or queries such as to the user.

Examples of physiological data include one or more of breathing related signals (rate, depth, and forced expiration, wheezing, coughing), cardiac signals such as heart rate, and changes in heart rate related to respiration (heart rate variability).

The user's medical records may indicate medication information, such as a medication or medications prescribed to the user, dosage information of same medications (e.g., then-current dosage instructions, a range of dosages depending on risk level, symptoms or severity, etc.), medications that the user may potentially be prescribed, and/or medications that the user should not be prescribed (e.g., due to allergy). The medical records may also include clinical records, such as physiological parameters measured and recorded by a clinician. Such information may be recorded in paper records, or an electronic health record (EHR), or electronic medical record (EMR) which is more suited to long term systemized trend analysis; a personal health record (PHR) is controlled by the patient, and is an electronic application for recording personal medical data.

The user feedback may be gathered from a questionnaire answered by the user and/or account information previously entered by the user, and may include such information as personal health information (e.g., are they a smoker, do they feel breathless and/or a feeling of chest tightness, and how do they feel after light, moderate and heavy exercise), medical history (personal and or family histories), height, weight, etc. It will be recognized that much of a user's feedback may also, or alternatively, be included in and gathered from the user's medical records.

Data from the treatment device 140 may indicate, for example, the type of treatment device, the medication provided therefrom, prescribed dosage information, the time or times at which treatment was administered, any notifications, failures or errors detected, and/or number of doses remaining in the device 140.

The system 100 further includes a management subsystem 120 connected to, or in communication with, the monitoring subsystem 110 and capable of receiving the data gathered by the monitoring subsystem 110. The management subsystem 120 is further configured to process the received data, and determine, based on such processing, onset and a degree of severity of a monitored condition, as well as an instruction (e.g., a prescribed dosage of medication) for treatment and prevention of the monitored condition. In some cases, the instruction (e.g., a prescribed dosage of medication) for treatment and prevention of the monitored condition may not be determined by the system, but received as an instruction from a third party.

The system 100 further includes an alarm subsystem 130 connected to, or in communication with, the monitoring subsystem 120 and capable of receiving the determinations made by the management subsystem 120 and alerting the user, clinician, or other device or person, based on the information received from the management subsystem 120. For example, if the alarm subsystem 120 receives an indication that the user is experiencing an increase in severity or frequency of the monitored condition, or requires treatment, or requires an increase in treatment dosage, the alarm subsystem 130 may be activated in response to instruct the user accordingly.

Activation of the alarm subsystem 130 may include any one or combination of a visual alert (e.g., via a display or light), or an audio alert (e.g., a pre-recorded message). Such alerts may be sent to either the user, a clinician, or both, as well as to other people (e.g., an emergency contact).

The system 100 may optionally also include a treatment device 140 that is used by the user to treat the monitored condition. In some cases, including when monitoring asthma and/or COPD, the treatment device 140 may be any one of an inhaler, nebulizer, oxygen supply, RPT etc. An electronic pillbox (e.g., recording/detecting the removal of specific medication from the box at a particular time for communication to the system) could also be connected. In some examples, the system may include multiple devices, and each device may be connected with the other subsystem components in the manner depicted in FIG. 1. It is noted that while the system is illustrated in reference to a single user who may be using one or more treatment devices, the system may be configured for multiple users, one or more of whom use multiple treatment devices.

Portable Disease Management System

Figure 2:
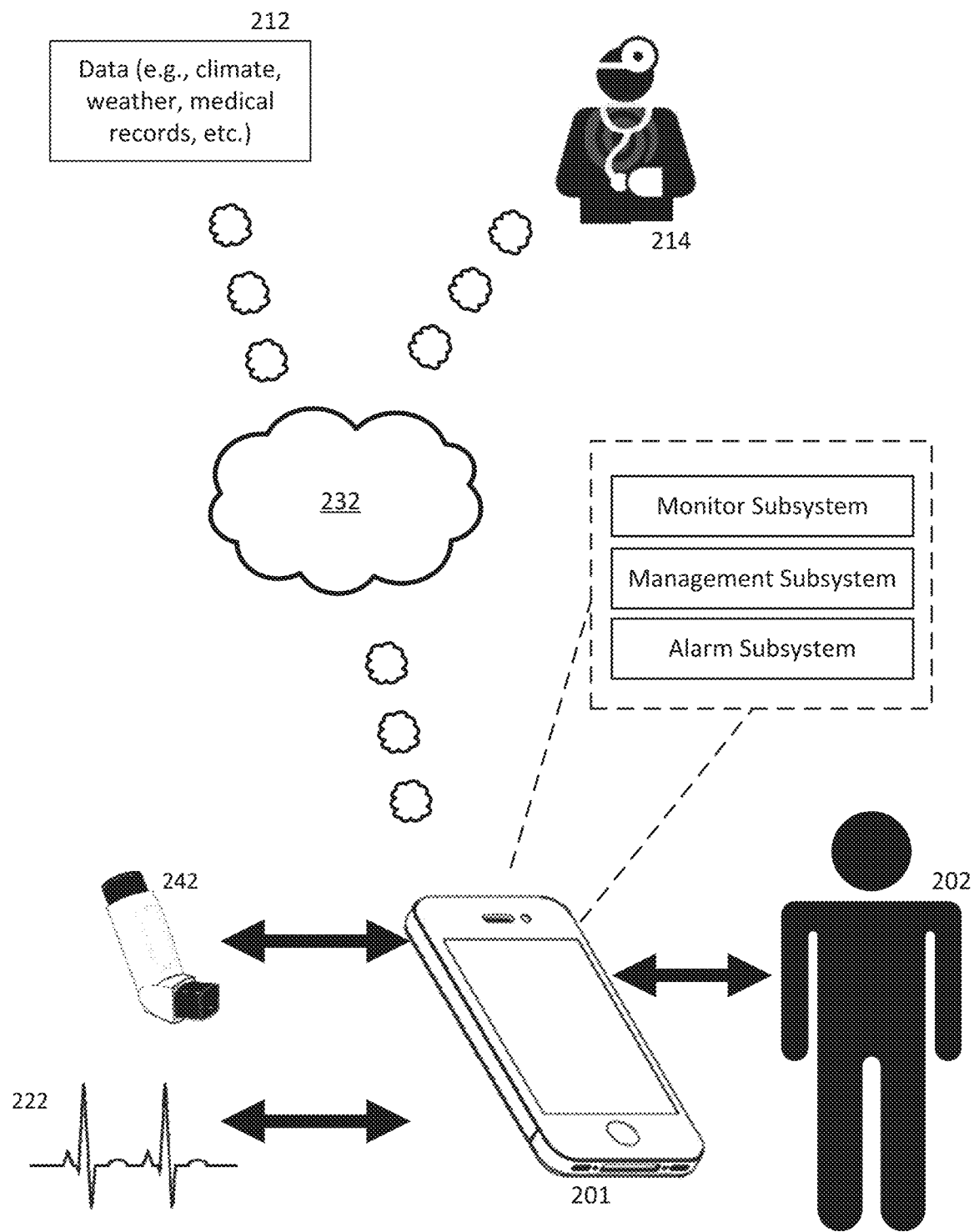
FIG. 2 illustrates a system for a patient with a smart device connected to a treatment device, a sensor, and various databases, in accordance with an embodiment of the present disclosure.

FIG. 2 depicts one example implementation of a portable system 200 in some versions of the present technology. In the example of FIG. 2, the monitoring, management and alarm subsystems 110, 120, 130 may be realized as one or more software programs or applications running on a portable device 201, such as of the user 202, such as smartphone, tablet, smart-watch, or other wearable or portable smart-device, with a processor and optional data link to a server. For a smart-device or other wearable sensor that can be operated by the user, such as a microphone, heart rate optical sensor, bio-impedance signals, galvanic skin response or accelerometer, such hardware may be interfaced with the software, and may be provided to the user at a relatively low cost (as compared, for example, with a standalone health monitoring device). Thus, the user's smart-device may be utilized as an apparatus for monitoring their own physiological data such that it may include, be, or communicate with, one or more such sensor(s).

The system 200 may utilize the peripherals of the device 201 in order to receive and transmit information (e.g., collect physiological data, sound an alarm, etc.). For example, the device 201 may be equipped with a microphone or other acoustic sensor (either within the device, or on an earbud/microphone cable, whereby the microphone is brought close to the user's mouth or be in proximity of the microphone's sensing capabilities) in order to record and process breathing sounds of the user. A microphone may further be used to monitor and classify sound patterns consistent with chronic cough or snore, and separate those noises from other background noises such as fans, road noise and the like.

Other examples of inbuilt or connectable sensors may include accelerometer(s) for step counting, a compass, a location positioning system (e.g., GPS), and heart rate spot measures. In the case of a smart-watch, the device may include sensors for monitoring heart rate (e.g., via optical or other methods), galvanic skin response, temperature sensing, blood pressure (e.g., derived from a photoplethysmographic signal), and/or breathing rate. For example, some devices, such as the Up3™ produced by Jawbone, may use bio-impedance measures to derive heart rate, respiration rate and galvanic skin response, by sending a small electrical current through the body and measuring tissue resistance to the electrical signal.

In the case of a smart-device, the smart-device may be equipped with a smart-case. The smart-case may provide an easy and portable way to keep medication with the user, since the smart-device is often within reach of the user. Medication, such as gaseous or powder inhaler, may be included in, for instance, a flat pack or cartridge included in the smart-case. The pack may include a mouthpiece (and, optionally, for connection to a separate adaptor piece). The pack could be replaceable, have capacity for several uses, and/or be capable of triggering a control signal based on a number of doses remaining. Thus, the smart-case may contain or couple to the smart-device and may serve as a housing or carrying case for any one or more of, for example, the smart-device, a treatment device, a sensor(s), etc. The smart-case may be configured for communication of data between the components of the smart-case and the smart-device, such as by wired or wireless communications (e.g., USB, NFC, Bluetooth, Wi-Fi etc.)

The smart-case may also provide an easy and portable way to integrate sensors with the user's smart-device. For example, the smart-case may include a respiration tracker, such as for sensing inspiratory/expiratory breathing phases of the user, in order to coordinate delivery of the stored medication with a large inspiration of the user. Similar sensing can also be used to act as a spirometer (a measure of pulmonary function), in order to measure forced expiratory volume (amount of air volume and how quickly exhaled). Gas sensing can detect carbon dioxide ($CO_2$) and nasal nitric oxide (NO) in exhaled breath. A heated thermistor for measuring end tidal $CO_2$, e.g., a non dispersive infra-red CO2 detector, could also be included. It may include a heart rate monitor (e.g., using sources such as LEDs, and with an electro-optical sensor).

The smart-case may draw power from a battery of the smart-device, or its own battery (e.g., a thin Li-Ion or lithium polymer, which may be flexible). If the smart-case includes its own battery, that battery may additionally function as an extended life battery for the smart-device. The case could also be powered by the smart-device, or have a coin-cell with low power Bluetooth LE or 3.5 mm jack with energy harvesting from an audio signal on one of the speaker channels (e.g., a 'Hijack' style implementation).

The device 201 may further be adapted to communicate with external sensors 222 using wired or wireless connections. For example, the device 201 and external sensor 222 may communicate with or use a radio frequency (RF) based link (e.g., a pulsed continuous wave quadrature non-contact sensor). The link may alternatively be via continuous wave (CW), frequency modulated CW (FMCW), UWB, passive detection from ambient environmental RF such as Wi-Fi or digital TV signals using received signal strength (RSS), or any other known means. These RF RADAR sensors when included may be used to measure movement, cardiac and respiratory signals from the biomotion of the user. For example, a smart-phone with such sensing or sensors in a smart-case (or indeed integrated into the smart-phone or tablet) could continuously measure these vital signs and movement when in the hand of the user, in a pocket, in a hand bag, or placed on a table or surface near the user (e.g., when placed on a desk as a user is working, placed on a table or chair arm, bedside night-stand, in a holder on an exercise machine, in a cup holder or other holder in a vehicle etc.). Communication could also be via USB, pin connection, NFC or similar. (Communication between a smart-device and smart-case could be similarly arranged.) The link may utilize a single or multiple antennas.

The device 201 may also be adapted to connect to a wireless network 232, over which the device 201 may be capable of receiving and transmitting additional information 212, such as climate data, weather data, medical records, etc. The system may optionally connect to medical information systems via the Health Level Seven (HL7) standard or a similar standard. The device 201 may also be able to communicate with people 214 or locations other than the user 202 over the network 232. For example, the device 201 may be capable of communicating an alert or receiving information to/from a physician, clinician or other person with information relevant to the monitored condition of the user 202.

The device 201 may also be adapted to communicate with a treatment device 242, including or in addition to the treatment device of an integrated case of the device (e.g., the smart-case described above). Any of the previously mentioned wireless or wired communication connections may be used to connect the device 201 and treatment device 242. For example, the device 201 may communicate over a wired or wireless link, e.g., to inhalers, nebulizers, capnograph, ASV, NIV, spirometers, or similar devices. If supported, the device 201 may adjust parameters (e.g., carry out dosage titration) of the treatment device 242 within a safe window (e.g., defined by a healthcare professional). The battery level and other operating and configuration parameters of the treatment device 242 may also be monitored.

In one example, the device 201 may receive and record a dosage delivered by a treatment device 242 (for example an inhaler or oxygen delivery system). The device 201 may also receive a manually configured dosage level (e.g., set manually by the user 202), for comparison with the dosage information received from the treatment device 242 such that the manually input information may override the information from the treatment device 242, or vice versa. The device 201 may also be capable of comparing the data from the treatment device 242 to a database of both subject specific and demographic data. The device may further update (or recommend an update to) the dosage delivered by the treatment device 242 (presumably provided that the updated dosage is within safe limits for the user, as defined or configured by a medical professional) based on any one of the above comparisons. The device 201 may similarly prompt the user 202 to increase their systemic medication if appropriate (this too may require the device 201 to contact a report physician service for approval).

Where the treatment device is an inhaler or other portable therapy device, a wireless interface between the device 201 and treatment device 242 may ensure that the device 201 stays within range of the treatment device 242. In the event the treatment device 242 goes out-of-range from the device 201, the device may provide an alert to the user 202 (audio, visual or vibration). The device 201 may also use the wireless interface to provide an alert to the user 202 in other scenarios (e.g., when the user has been stationary for some time and then begins to move, when an elevated risk is detected, etc.) to remind them to bring, or not to forget, the treatment device 242. The device 201 may optionally pre-set an inhaler over the wireless interface based on detected patterns, as well as counting puffs (uses of the inhaler), and communicate such data to a remote system, e.g., via the network 232. The wireless interface may operate in a battery powered mode (e.g., low power Bluetooth LE/Smart in, for example, beacon mode). The interface may also use such services as iBeacon (part of Bluetooth LE) to provide both basic indoor navigation and proximity sensing.

If the treatment device 242 is a smart inhaler or smart drug delivery mechanism via a mask, it may also track user compliance, e.g., detecting the expected resistance to puff of a person correctly taking the dose on an inspiration, and may interface with the device 201 to notify whether medication was taken correctly or incorrectly.

If the treatment device 242 is an electronic pillbox, it may also track administration of medication stored therein (e.g., of a systemic asthma treatment (e.g., a bronchodilator), automatically releasing a diuretic treatment for CHF, an antibiotic for COPD, or other prophylaxis such as an antihistamine, etc.).

Lifestyle Management System

Use of a portable device to conduct monitoring of the user's condition is especially beneficial in that the portable device may be kept with the user at all, or at least most, times. This availability of the user for monitoring thereby enables the portable device to gather information relating to the user and the user's condition on a 24-7 (continuous) or near 24-7 basis, and to conduct similarly regular analysis regarding the user's current health and future health risks. In this regard, the device may be considered as much capable of performing lifestyle management for the user as merely screening the user for health risks.

Figure 3:
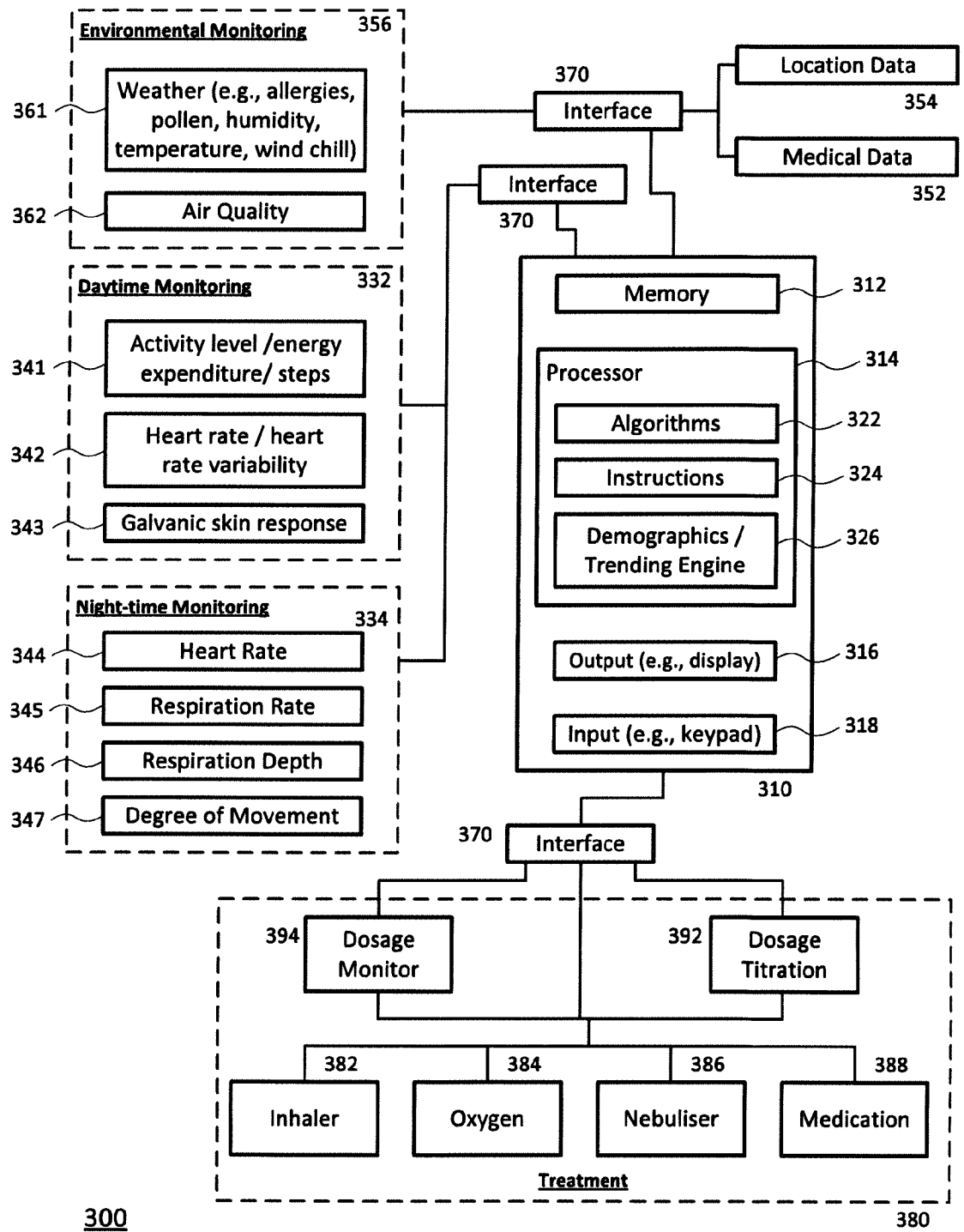
FIG. 3 further illustrates components of an example of the system of FIG. 2.

FIG. 3 depicts one example implementation of a lifestyle management system 300 in accordance with some versions of the present technology. In the example of FIG. 3, the system 300 includes, or is associated with, a portable device 310 that may be carried by the user, a plurality of sensors and monitors (341-347 and 361-362) operative to sense physiological and/or other parameters relating to the user's monitored condition, one or more treatment devices 380, and one or more external systems (352, 354) that are communicatively connected to the portable device 310. The sensors, monitors, treatment devices, and other external systems may communicate with the device 310 over various interfaces 370 (e.g., RF link, NFC, wireless or wired network connection, etc.). It should be noted that any or all of the elements indicated in FIG. 3 may be an integral part of the system 300. Additionally, any or all of the indicated elements may be third party hardware components, brought together by a software-based application that may, for instance, be used to configure the portable device 310 to communicate with any of the remaining components, so as to facilitate the described functionality of the system.

The portable device 310 of the lifestyle management system 300 includes a memory 312 and processor 314, which itself may contain algorithms 322 for performing any of the analyses described throughout this specification, as well as instructions 324 for carrying out any of the functions described throughout this specification. The processor may also include hardware, or access software from memory, for a trending engine 326 for analyzing trends and/or user demographics (discussed in greater detail below). The portable device may also include an output interface 316 (e.g., a display, vibrator, speaker, LED or other light, etc.) capable of providing information and instructions to the user, and an input interface 318 (e.g., keyboard, buttons, microphone, infra-red scanner, accelerometer, etc.) capable of receiving data and commands from the user. As in the example system of FIG. 2, the portable device 310 of FIG. 3, may, for example, be a smart-device, such as a smart-phone or smart-watch.

The physiological sensors and monitors of the system 300 may be classified into two groups: daytime physiological monitors 332, and nighttime physiological monitors 334.

The daytime monitors 332 may be adapted to monitor physiological parameters of the user even when the user is away from their home or out of bed. When the user is out of bed, their physiological parameters can optionally be monitored by a body worn sensor. The sensor may be a clip based device, stick on patch (dermal or lab-on-chip) or wristwatch style device. For example, the user's activity (e.g., activity levels, energy expenditure, a step counter, etc.) may be monitored using such an activity sensor 341 (e.g., accelerometer). Likewise, the user's heart rate (as well as heart rate variability) and galvanic skin response may be monitored (e.g., by optical, electric or movement means) by a properly equipped respective devices 342 and 343 regardless of the user's location, provided that the user has taken the device along. Overall, the above "daytime/waking monitoring" is targeted at monitoring the user in their waking activities.

Heart rate (HR) data may be gathered from a user on a continuous or semi-continuous basis. Such data gathering may be conducted via a chest band (e.g., a sports monitoring band such as provided by Polar® or similar), or a wrist watch implementing heart rate monitoring (e.g., Basis watch, FitBit®, ambulatory ECG, photoplethysmogram, or the like). In some cases, a low user impact device, such that is suitable for daily monitoring over an extended period of time (e.g., days, months, years) may be used.

Galvanic skin response (GSR), also known as electrodermal response, may too be recorded by a wearable device (e.g., the Basis watch, or other commercially available GSR measurement devices). The GSR signal is used as a surrogate measure of sympathetic "fight or flight" activation.

For those examples for which skin temperature is analyzed, skin temperature may be recorded, for example, by a wearable device with a temperature sensor.

The nighttime monitors 334 may be adapted to monitor physiological parameters of the user when the user is home or in bed. For example, if the user is in bed, a bedside (or under-the-bed) non-contact or minimal contact monitor may be utilized to collect physiological parameters such as heart rate 344, respiration rate 345, respiration depth 346 (e.g., shallow/panting, deep breaths, or breath cessation or diminution), degree of movement 347 and other associated parameters. In some examples the nighttime monitor may be any of a radio frequency (RF) monitor, accelerometer, piezoelectric or UWB (Ultra Wide Band) mattress. Passive infra-red monitors, or other optical means such as a camera with skin color and movement detection, may also be utilized. Thus, using the combination of daytime and nighttime monitors, the system 300 may be capable of 24-7 monitoring of the user in order to better monitor and assess the overall lifestyle of the user.

In a bedroom setting, heart rate may be estimated based on sensors other than the above example daytime sensors. For instance, a user may wear a contact (e.g., a wearable device such as the Basis watch or ECG electrodes and device) or one or more non-contact sensors such as one or more ResMed RF sensors, using techniques such as wavelet based time-frequency transforms. Wavelets are a time/frequency approach for analyzing signals at different time scales. For example, a discretized continuous wavelet transform (CWT) may be utilized (using for example Daubechies Wavelets) to separate each of the cardiac and respiratory components of a biomotion signal, thereby exhibiting a strong de-noising behavior. For example, signal analysis in some versions of the present technology may include any of the methodologies described in International Patent Application Publication No. WO2014/047310, the entire disclosure of which is incorporated herein by reference, including, for example, methods of wavelet de-noising of respiratory signals. Examples of such sensors include RF motion sensor described in in U.S. Patent Application Publication No. 2014/0024917, the entire disclosure of which is incorporated herein by reference.

In the case where one or more RF sensors are implemented, the sensor(s) may be any of the sensors, or multiple coordinating/coextensive sensors, described in U.S. patent application Ser. No. 14/415,677, filed on Jan. 19, 2015, U.S. Provisional Patent Application No. 62/205,129, filed on Aug. 14, 2015, and U.S. Provisional Patent Application No. 62/207,670, filed on Aug. 20, 2015, the entire disclosures of which are incorporated herein by reference. Moreover, such sensors may be configured for detection or identification of biometric characteristics to discriminate particular individuals according to any of the methodologies described in U.S. Patent Application No. 62/207,687, filed on Aug. 20, 2015, the entire disclosure of which is incorporated herein by reference, such as for aggregating sleep information in relation to a particular or single user where multiple sensors are employed.

Blood pressure parameters may also be derived from a wearable photoplethysmography based sensor.

Although the above sensors have been classified as "daytime" and "nighttime," it should be recognized that any of these sensors may be utilized by a user at any given time of day, and that the user is capable of wearing many of the "daytime" sensors to sleep, as well as carrying around a "nighttime" sensor during the day.

For example, it is recognized that as a person with chronic diseases becomes sicker, they will (i) tend to move around less (whether in their home, nursing home, hospital etc. and outside), (ii) have fragmented sleep, and (iii) that they may choose to sleep with extra pillows on their bed or sleep in a chair near their bed, or in another part of the house (e.g., a living room). The third point is especially true with worsening congestion, as sitting up can make it easier to breathe. This does pose a challenge in terms of monitoring the person's sleep and other signals, which can be addressed by systems that allow multiple sensors to coexist together (such as described in U.S. Patent Application No. 62/207,687), and also to detect the biometric characteristics in different locations (such as described in U.S. Provisional Patent Application No. 62/207,687), and relate to person being monitored. How this works is as follows.

The system may be capable of distinguishing between two or more subjects in a room, and identifying a particular person using contactless sensors. For example, the system may process movement features, activity features, heart ballistocardiogram features and/or breathing features. Such methods can be applied to active RF sensing systems such as continuous wave (CW), pulsed CW, frequency modulated frequency modulated continuous wave (FMCW), frequency shift keying continuous wave (FSKCW), frequency hopping, and ultra-wide band (UWB) systems. Sonar methods using CW, pulsed CW, FMCW, FSKCW, frequency hopping, and UWB schemes with inaudible (to most humans) 18-22 kHz range signals can also be utilised. The FMCW approaches in both types of sensors can use a variety of modulation schemes such as ramp (chirp) signals, triangular, sinusoidal.

A person has a chronic disease (say CHF) and sleeps with a bed partner, both of which are monitored in the bedroom using two smart RF sensors that are designed to coexist together, and also to detect and recognize the biometrics (identity) of the persons being monitored. The person also wears a smart wrist watch monitor containing sensors during the day, which they dock at night to charge. As their condition worsens, the person spends most of the night in an adjacent living room on a comfortable reclining chair. The house can contain several RF sensors that are either plugged into AC outlets (which may act as pass through AC mains outlets, in order that the outlet/socket can still be used by other equipment), or into USB sockets as pass through or hubs. These other sensors can communicate via a mesh network, over the cabling, or via Wi-Fi, Bluetooth etc. A sensor can be located in the proximity to the chair where the user is sleeping and the system can detect the biometric data of the user. It can then combine the sleeping sections from the bedroom and later from near the chair, associated with that user, and also extract the heart and breathing signals. Thus, different sensors may be employed to detect physiological parameters from different locations (e.g., different rooms where a person might spend time such as a bedroom or near-bed sensor and a sensor in another room other than the bedroom).

The system can determine a location of the user (e.g., based on a signal from the user's device) and based on the determined location, can receive physiological parameters from a sensor in the determined location. The system may further disregard data collected by sensors in locations where the user is not located. Thus, even if a second user moves over to "the warm side of the bed" vacated by a first monitored user, the system can exclude the biometric data of the second user in analyzing the physiological condition of the first user (and/or process the biometric data of the second user separately from the data of the first user). Furthermore, the system can differentiate not only between users, but also between humans and animals, such as a user and the user's pet dog, for example. This helps the system avoid the inadvertent detection of and data collection from pets in the property.

It is also possible to monitor bathroom areas for falls/slips. For the first user, it can also combine with the signals gathered by the wearable device during the day (or indeed from the sleeping period, if the user chooses to wear; such a device might include an oximeter which could provide useful information on oxygen saturation over one or more nights). It can be seen that it is possible to detect desaturations from a wearable oximeter (e.g., classic finger probe, ear lobe, sticking plaster, wrist worn, placed in CPAP or other mask form factor). Additional monitors may gather non-physiological data. The non-physiological data may be gathered over a network or other connection. For instance, as a location of the user 352 may be determined by GPS or other positioning data. Medical data 354 and environmental data 356 may be accessed over a wireless network (e.g., during daytime), or through a wired network (e.g., at nighttime), or combination thereof. In some cases, environmental data may also be accessed without a network (such as if the device 201 has a built in thermometer).

It is noted that home based sensors can be configured to detect smoke or other particulates or pollutants in the home and raise an alert. They may also be configured to detect trace amounts of cigar/cigarette smoke (below the thresholds of a commercial smoke/fire detector) to check compliance with a smoking cessation program (e.g., has a user with COPD actually given up smoking). Other types of sensors may be used to detect dusty environments or volatiles in the air that might trigger an event (i.e., to detect known personalized triggers, and to suggest remedial action to reduce or remove the trigger to the user or to a monitoring service for external intervention).

The environmental data 356 may include weather data 361 (e.g., allergy levels for various allergens, pollen levels, humidity data, temperature, wind chill, etc.), such as from various online sources, as well as air quality information 362 from local air quality sensors. Such data may be obtained from wired or wireless sensors, or via 'online' services such as local, regional and trending sources of weather, air pollution, and allergy (e.g., pollen) conditions data.

More specifically, short and long term weather data may be obtained from a variety of online sources. Allergy alerts (e.g., related to pollen count) may be determined based on either forecasted or seasonal values. Allergies may also be determined or identified as part of subjective questionnaires (e.g., questions presented to the user by a software application). Other environmental data (e.g., information relating to air particulates and pollen counts) may similarly be estimated or gauged based on subjective input of a user.

In addition to external sources of environmental data, temperature, humidly, and air quality data may also be accessed from domestic environmental monitoring systems, such as sensors in a house.

Returning to the trend monitoring engine 326 (software and/or hardware) of the portable device 310, this component of the system 300 may be configured to analyze received or accessed data to determine whether there is an increased risk, or risk of exacerbation, of a monitored condition such as asthma or COPD. In this regard, trend monitoring may involve creating a map (e.g., a decision tree, a geographical map) of asthma and COPD risk factors, such that the system is configured to provide feedback to the user to enable self-management of the condition. To provide such feedback, the system can leverage a device that the user carries around with them all or most of the time (e.g., their smart-device—phone and/or tablet and/or wearable interface such as a wristband, clip on device or smart garment) in order to allow the user greater freedom, with reduced uncertainty and anxiety, while gathering a large quantity of data relevant to the monitored condition. As discussed below, the system can then also be configured to guide the user, such as by providing/generating audio, video, pictures and/or text messages, to conducting behaviors that will reduce their risk of an attack/exacerbation, and can further be integrated with existing therapy—for example as part of a PAP device or active smart mask.

Trend monitoring may involve learning from a wider set of data, derived from the broader population, about risk factors; such risk factors may be localized areas of airborne irritants, seasonal factors, local weather factors (including forecasting data), room environmental data, exercise levels, breathing patterns, cardiac patterns (including breathing waveforms and acoustic characteristics such as cough, sneezing and wheezing), changes in skin temperature, skin coloration, sleep quality changes, and blood pressure. Additionally, the system can learn subject specific triggers (e.g., a state of affairs represented by collected data that lead to an exacerbation event(s) for the user) that may not be seen in the wider population, by utilizing feedback from the user (e.g., from a questionnaire).

If trends are recognized that are indicative of a worsening of condition (e.g., a risk factor for an asthma attack or a COPD exacerbation), then the system can proactively alert the user and/or medical system, and suggest a course of action—which may include adjusting equipment and/or treatment parameters. Some monitoring devices and processing methodologies capable of using various measurements to detect a condition exacerbation are described in International Patent Application Publication No.

WO/2013177621, the entire disclosure of which is incorporated herein by reference. Once an adjustment or parameter is determined, relevant information may be presented to the user on a screen, via visual indicators, and/or via audio cues.

The device 310 of FIG. 3 may be further in communication with one or more treatment devices, including an inhaler 382, oxygen supply 384, nebulizer 386, or other medication 388 (e.g., in a pillbox or other medication dispenser with an electronic chip, such as an RF identification chip). The means for communication with the treatment devices 380 may be any of the previous describes connections or links described in relation to FIG. 2.

Additionally, in FIG. 3, the device may be configured to interface with one or more devices for dosage monitoring 392 and dosage titration 394. The devices may be integrated with the treatment devices 382-388 (as described in relation to FIG. 2), or may be a standalone interface between the user's device 310 and the treatment devices 382-388.

Monitoring Chronic Disease

Figure 4:
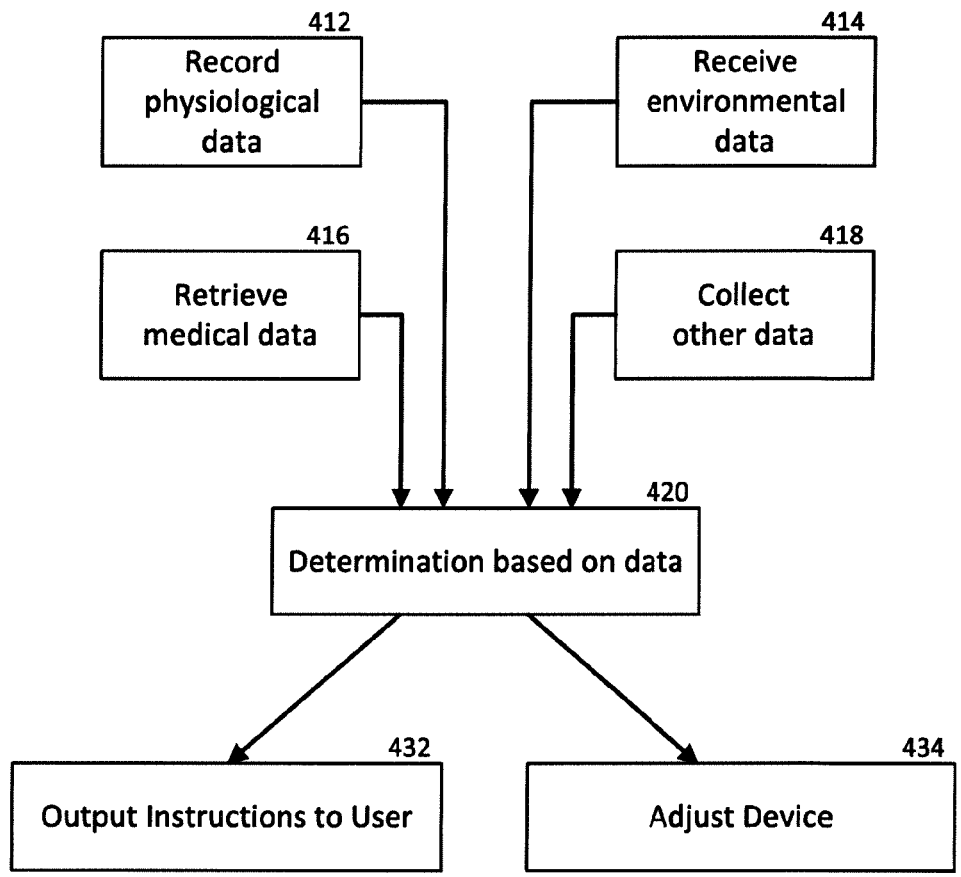
FIG. 4 shows example processes for a method of monitoring and managing a chronic disease of a patient in accordance with one or more versions of the present technology described herein.

FIG. 4 provides a high-level depiction of a method for monitoring and managing a chronic disease condition of a user of any of the above described systems, or a similarly designed system. In FIG. 4, the system collects various types of data pertaining to the user's condition. Such data collection may include recording physiological data (at 412), receiving environmental data (at 414), retrieving medical data or records (at 416), and/or collecting other data (at 418) such as the user's location.

At 420, the system makes a determination about the user's chronic condition or an associated treatment, based at least in part on the gathered data. Such determinations may include detecting a current severity of the condition, detecting or predicting a risk for exacerbation of the condition, determining a current course of treatment for the condition, and so on.

If the system includes a demographics engine, trending engine, or the like, at 420, the system's algorithm may extract a plurality of parameters related to the condition of the user based on the data gathered at 412-418. Extraction of the parameters may be performed using time and/or frequency analysis techniques. Then, some or all of those parameters may be analyzed based on additional information from a database containing data from both healthy and disease state subjects. The database may also contain demographic data as an extra source of information for cross referencing.

The system may act upon the determination made at 420. Such actions may involve one or more of the activities previously described in relation to an alarm subsystem or output interfaces of a user's portable device. For example, the system may provide instructions to the user (at 432) regarding treatment, treatment dosage, refraining from strenuous activity, etc. For further example, the system may directly adjust a treatment device (at 434), for instance making an abrupt adjustment in the dosage level, or setting a titration of the dosage level, to provide an updated level of treatment to the user.

The system may also recommend non-medical actions. For example, a person in a pre-exacerbation phase of the condition may be instructed to undertake relaxing breathing exercises such as meditation, to reduce anxiety. Alternatively, or additionally, the system may provide guidance to the user to improve their sleep hygiene in order to improve sleep quality. For further example, if the user is a smoker and local air quality sensors detect a decrease in air quality, an alert may be provided to the user not to smoke. In other words, air quality sensors may be capable of detecting particles such as from smoke and other sources. Thus, these sensors may be leveraged to generate a reminder to sufferers that they should avoid cigarette smoke (for example), or to use a daytime mask or nighttime flow generator with filtering. Room air filtration systems could also be installed. Such alerts may be powerful behavior modifiers for a pre-asthma or asthma sufferer, and may encourage them to give up smoking in order to reduce their risk of developing COPD.

Where cold air is a specific trigger, a mask system with a gentle heating element may be used (e.g., on a CPAP or a mask including air filtration work outside on the street), or a control signal sent to a controller of an air handling system such as air conditioning or heating system to adjust the temperature to minimize the risk of an exacerbation. In fact, staying indoors with an air handling system (air conditioning, air purifier, active or passive mask) to maintain moderate temperature and a relative humidity of around 40% may be one of the few ways to reduce risk (assuming that the indoor environment is low in dust).

The following are examples of analyses that may be carried out by the systems described above. The methods described herein may be performed, entirely or partially, by an automated system may in order to optimize the quality of life of the user.

Physiological Signal Analysis and Processing
Cardiorespiratory/Autonomic Analysis In order to determine physiological parameters including respiratory rate, respiratory stability and respiratory depth, a number of approaches may be implemented by the system.

A ballistocardiogram is related to pressure waves apparent at the skin surface due to cardiac contraction. For example, for a baseband signal from an RF sensor or from other sources containing ballistocardiogram and respiratory components, a pulse shape filter (such as a matched filter) may be employed, such that when a high correlation is detected with a template, a peak finding operation can be performed to identify and extract a beat or breath.

Other methods can perform direct peak/trough or zero crossing detection in the time domain with adaptive thresholds to track changing amplitudes of the ballistocardiogram (or ECG) signal. The decision making process may be augmented using spectral analysis, such as a DFT (discrete Fourier transform) in a sliding window, in order to localize a breathing trace, even in a relatively noisy input signal (e.g., a hybrid time/frequency approach). The DFT may be implemented using a Fast Fourier Transform (FFT). Thereby, it is possible to track changes in breath rate and/or heart rate (e.g., search for areas of elevated heart rate, search for areas of elevated or shallowed breath rate, or areas of more rapid or less rapid breathing than normal for a predetermined average person (shallow breathing may be indicative of dyspnea)).

A process may be implemented to detect patterns in breathing (respiration) rate, and may further detect changes in the respiration dynamics of a user. Such changes may be seen even days before a worsening of the monitored condition. Such a process may include, for example, one of the algorithms 322 for detecting inspiration, expiration, and/or the expiratory/inspiratory pauses. For example, the algorithm may adaptively track a baseline respiration rate, movement characteristics and breathing waveform shape of a person over days, weeks, months or years to build up a profile of their respiration dynamics (e.g., of change in rate and depth over time). Where benchmark measures such as spirometer parameters are available, respiratory depth estimates from a wearable or non-contact sensor can be calibrated to the estimated tidal volume; if such calibration is not available, relative measures of depth can still be calculated over time (multiple days or longer periods) in order to detect increasing (or decreasing) shallowness of breathing. The algorithm may then estimate a probability of a worsening in condition based on the tracked profile. In this manner, the algorithm may be capable of predicting the worsening of the condition even before the worsening requires clinical intervention. Comparisons may include data from similar users (e.g., users of a common demographic or having common patterns in their tracked data points), and particularly the observed disease progression for those users, in order to estimate a likelihood that a specific person will suffer progression (e.g., worsening) of a specific disease.

The algorithm module may create an adaptive baseline for a user, and can look at breathing rate parameters such as median, mean, interquartile range, skewness, kurtosis, minimum and/or maximum breathing rates over a predetermined period of time (e.g., 12 hours, 24 hours, 48 hours, etc.). In some examples, the algorithm may target those times during which a person is asleep. In addition, the algorithm may track inspiration/expiration waveform shapes, as well as short, medium and long term breathing fluctuations. For example, it is believed that an average breathing rate of 24 or more breaths per minute may be indicative of a serious medical condition. Thus, a threshold of 20 breaths per minute may be used to trigger a first alert (e.g., an 'orange' alert) indicating that the monitored patient is probably unwell, and a threshold of 24 breaths per minute may be used to trigger a second alert (e.g., a 'red alert) indicating that the monitored patient is likely to be critically ill. These thresholds may vary from person to person, as for example a stable COPD subject may have a relatively high average breathing rate, but still be in a steady state as far as disease progression is concerned. The baseline fitness of the user may also impact the analysis of these readings.

With respect to heart rate, it has been found that COPD subjects, as compared to people who do not suffer from COPD, exhibit relatively rapid heart rate variability (HRV) at high frequencies (indicative of short term fluctuations) during exercise. This may be due to impaired cardiac autonomic regulation. Similarly, COPD subjects may exhibit relatively higher overall HRV after exercise. HRV or RSA (respiratory sinus arrhythmia) is where the heart speeds up during inspiration, and slows down during expiration. Higher overall RSA may be considered as an indicator of being healthier.

The HR data may be analyzed to produce heart rate variability (HRV) estimates. Recorded HRV parameters (such as short term and long term fluctuations of heart rate) may be compared to trends or patterns in past data, as well as to demographic (expected) parameters for both healthy subjects and subjects with chronic disease. Identified features may be provided to the classifier.

In some cases, a smoother version of the HRV may be utilized for the analysis. The smooth HRV may be derived based on low pass filtering of the HR data. Smoothened HRV data is generally used for analysis of relatively long term fluctuations, such as for detrended fluctuation analysis.

It is noted that such detrended fluctuation analysis (DFA) may also be suitable for detecting changes or change points in parameters monitored over multiple days (or longer time periods such as weeks, months or years). Such an approach suggested to be particularly suited to non-stationary signals, and acts as an estimator of the statistical self-affinity of a signal. For example, a multiple measure of breathing rate and/or heart rate such as the median or $75^{th}/90^{th}/95^{th}$ percentile can be processed using DFA in order to detect significant change points.

Many of the above inputs may be combined in a manner that yields further data and enables further analysis. For example, combining extracted GSR and HRV signals may yield an estimate of the ratio between sympathetic and parasympathetic activation. The estimated balance of sympathetic to parasympathetic activity may be used to estimate stability or progression of a potentially-worsening condition, such as COPD.

Skin Temperature

The skin temperature data may be analyzed in combination with breathing rate and/or heart rate data. For instance, if an increase in skin temperature is detected along with a subsequent or simultaneous increase in breathing rate and an initially stable heart rate which subsequently becomes elevated, such detection may be an indication of an onset of a virus or bacterial infection, and thus sickness. It is noted that such changes may also be detectable from patterns in cardiorespiratory data, even where skin temperature is not available.

Movement, Exercise and Falls

With respect to exercise intensity and duration, such data may be captured from the daytime monitors described above. The captured data may further recorded to a database, where the data may be analyzed for specific trends and/or variations. For example, the system may determine that the user is relatively inactive, as compared to the user's trends or to other users. Such a determination may be associated with a loss of physical condition (which itself may reciprocally cause further deterioration of the user's physical condition), reduction in functional capacity, and/or exertion related dyspnea (shortness of breath).

Energy expenditure may be estimated based on a combination of heart rate data, GSR data, and step counter data (e.g., from a pedometer). Alternatively, a standalone step counter may be used as a surrogate of exercise intensity (e.g., using a Nike Fuelband, FitBit, Jawbone, Misfit or similar wearable device).

Physiological motion may be analyzed, for example, in a bathroom/toilet or bedroom environment, and may be determined using the above described monitors as well. The monitors may detect unusual patterns such as slips and falls. RF sensors, in particular, are well suited to detecting movements in a space—e.g., in a room in the field of a sensor. For example, an RF sensor may be used to detect characteristic fall patterns. In the case that a characteristic fall pattern is detected, the detection may trigger an alert signifying a fall, e.g., from bed, from a bathroom/toilet, etc. The motion sensor and associated sensing field may be arranged such the user is more likely to fall in the sensing field (e.g., out of bed on the side of the sensor). More generally, the motion sensor may be positioned in such a way that a large amplitude/rapid motion signal indicates a gross movement, and that a breathing signal may also be detected from the subject.

Detecting a fall may be based on a combination of data from the motion sensor and another monitor. For example, a large movement (gross movement) detected by the motion sensor in combination with a change in amplitude from a breathing signal may be indicative of a fall. Threshold levels may be determined for both signals, for example based on previous data for the user or for other users. The measured movement and/or respiratory amplitude can then be compared with the respective threshold. A secondary capacitive sensor may be used to augment the detection in a specific region (e.g., a short range contactless capacitive sensor may be placed to the side of bed where a fall is most likely, such that if the subject falls and stays in range of this sensor, a fall alert may be triggered by the system).

In another example system, the user may be expected to traverse a specific region of the sensing field when getting out of bed normally. Thus, if the expected traversal is not detected, but the motion sensor indicates a large movement, a change in position, or the breathing/vital signal(s) disappear, such event(s) may be considered as an indication that the user may have attempted to move, but has fallen. A fall detection and/or alert may then be triggered.

The motion sensor(s) may also be used to detect a user rolling over in bed. For rollover, there are characteristic changes in amplitude of a movement and/or breathing signal, e.g., of a non-contact biomotion signal. For example, the envelope of the signal (e.g., estimated with a peak hold or Hilbert transform approach) may provide an estimate of the relative amplitude of breathing. Using such an estimation, a large amplitude in breathing may be associated with those cases for which the torso of the user is facing towards a monitoring sensor (e.g., the user lying on their side facing the sensor), and smaller amplitude for those cases in which the user is on their back (e.g., chest perpendicular to sensor), and yet even smaller again in those cases for which the user is lying on their stomach or on their side facing away from the sensor. Such amplitudes (and changes thereof) may be related to the moving surface area of the user's chest during breathing, and thus may vary based on the user's position relative to the sensor (or multiple sensor modules). Again, one or more threshold levels may be determined for the amplitude of the respiratory signal, for example based on previous data for the user or for other users. The measured respiratory amplitude can then be compared with the determined one or more thresholds, in order to estimate the likelihood that the user is a specific position in bed.

In yet other example systems, additional algorithm processing steps (and associated digital signal processing steps) may be included for determining repetitive and varying motion, including motion caused by movement of one's chest due to respiration, sway motion detection, sway motion cancellation detection, rollover in bed, and gross and fine movement detection due a multitude of actions including scratching (e.g., due to physical irritation or discomfort) are processed.

For one example system including in-bed monitoring, the system may analyze two channel (in phase and quadrature) signals recorded by a radio frequency RADAR that have been digitized using a suitable ADC module. These RF signals may be continuous wave or pulsed (e.g., applied to ResMed's SleepMinder™ 5.8 GHz or 10.525 GHz sensor, devices utilizing frequency modulated continuous wave (FMCW) methods, UWB, RSS or others). The signals may be fed into a filter bank, whereby a series of digital filters including bandpass filtering may be applied to detect and remove low frequency sway information. The phase information in the two channels may further be compared to produce a clockwise/anti-clockwise pattern.

Hysteresis and glitch detection (e.g., to reject non-human motions, or to detect periodic limb movement) may also be applied in order to suppress signal fold-over, and to determine whether a movement is moving towards or away from the sensor, as well as whether the movement is changing direction. Peak/trough detection and signal following may additionally be used to aid this processing.

Calculation of spectral content of a signal may be performed using a Fast Fourier transform using either find peak (frequency domain) or time-frequency processing comparable to processing using a discretized wavelet transform, appropriate basis selection, or peak find. The residual low frequency components identified in this process may also (e.g., separately) be processed to determine longer timescale trends.

Coughing, Wheezing and Snoring

Figure 5:
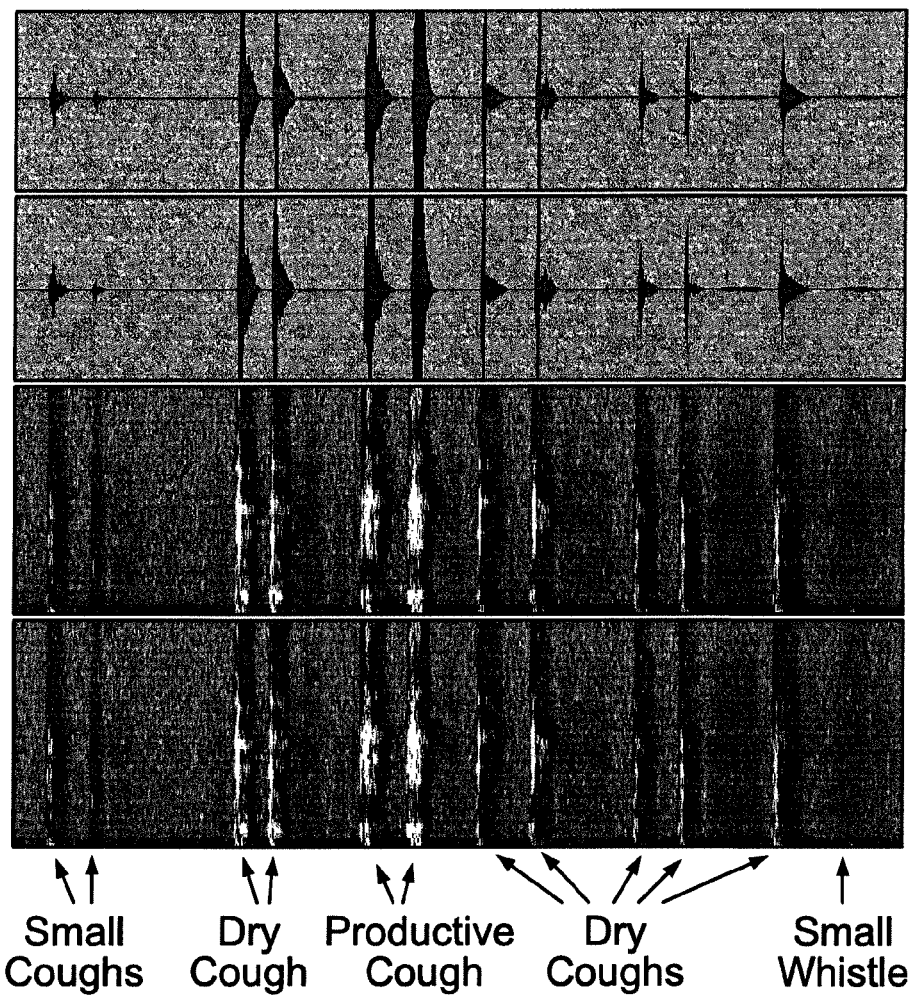
FIG. 5 is a time domain (top) and frequency domain (bottom) graphical representations of recorded audio data including sounds from various types of coughs and wheezing.

Coughing and wheezing may be detected using an acoustic sensor, such as a microphone. For example, high pitched whistling, which may be characteristic of or related to turbulent air flow seen, for example, in asthma patients, may be picked up by a microphone. Additionally, the coughing (either dry or productive) may be sensed using a microphone. Examples of audio data of coughing and wheezing captured using a microphone, and their respective distinct features, are shown in FIG. 5. Alternatively, or additionally, an RF sensor may be used to detect coughing.

The system may be capable of detecting the characteristic patterns of snoring, snuffling, coughing or breathing difficulties. Detection may be implemented using a digital filter bank, frequency decomposition, a search for 'bursty' noise (e.g., a "cough signature" using spectral analysis) and/or morphologic processing. These events may optionally be cross-correlated with patterns identified in sensed movement and/or respiration data.

The system may analyze the coughing/wheezing/snoring data for patterns and/or trends over multiple nights. For example, in the case of COPD, one suffering from COPD may experience reduced sleep time and increased arousals over a duration of time. Thus, a trend in such a direction may be indicative of an increased risk of COPD or exacerbation of a preexisting COPD condition.

Some or all of the extracted respiration, heart rate, movement, and coughing and snoring parameters may be utilized to estimate the number of apneas and hypopneas occurring during a sleeping period. Detection of coexistent COPD and OSAS (overlap syndrome) may be associated with more severe hypoxemia. This may for example be indicative that the user requires treatment using a CPAP, auto servo ventilation (ASV) device or other therapy or medication.

A cough can be considered to include an opening of the glottis (the explosive sound), followed by an expiration, followed by a closing of the glottis. A cough can also be classified in terms of whether it occurs in spasms (e.g., continuous coughing for longer than approximately five minutes). A cough can yet further be classified in terms of its productivity, or in other terms whether the cough is dry or wet (e.g., the presence of mucus indicating a productive cough). The expiratory time (e.g., measured based on the audio signal, measured based on the contactless respiratory signal, measured based on movement of the chest) of a productive cough is typically longer than the expiratory time of a dry cough.

A cough can also be classified in terms of whether it is chronic. A chronic cough is generally considered as a cough lasting for longer than two months, and may also be referred to as a persistent cough. In asthma, typically dry coughing with wheeze is observed. Cough variant asthma is thought to be a precursor of classic asthma. In gastroesophageal reflux disease (GERD) coughing is usually dry, and occurs in spasms. In COPD, coughing is usually productive, producing large amounts of mucus. Upper airway cough syndrome (UACS) is related to upper airway conditions.

In cases of chronic cough, the monitored respiratory signals can be used to estimate sleep disordered breathing (SDB), for instance to check for undiagnosed SDB, or to monitor the treatment of previously diagnosed SDB where CPAP therapy is in use. GERD and associated GERD cough, seen more often in women, has a high concordance with SDB. Specific system-generated recommendations for a detected GERD cough can include a selection of medication(s) to reduce acid production in the stomach.

If a cough occurs at night while the subject is trying to sleep, the cough may be detected by any one or combination of a disturbance in the breathing signal, a change in heart rate (typically an increase sustained for a period after the cough, primarily during exhalation), an increase in blood pressure, and a gross motion event (e.g., due to mechanical movement of the chest). Over the night a reduction in sleep score may be seen, especially if cough spasms occur. Depending on the type of cough that occurs, a pattern of large inspiration followed by large expiration followed by large inspiration may be seen. In contrast, other types of cough may be emphasised by a large explosive expiration followed by inspiration breath—large expiratory rise time, plateau, then a recovery breath (or just a large expiration). The "spikes" induced in the respiratory waveform can result in an increased estimated breathing rate, or in some cases a decreased breathing rate over a short timescale. Therefore, in addition to estimating breathing rate, the waveform may be analysed by processing local changes in breathing amplitude changes via estimation of the envelope of the breathing signal, and tracking individual parts of the inspiration/expiration waveform morphology.

The system checks if is there a progression to full, sustained wakefulness related to a spasm of coughing. This pattern may be evident from either or any combination of a contactless sensing signal (e.g., (RF, SONAR, optical), the audio cough signature, and cough repetition rate. Coughs during REM/deep sleep are rare (and even more unlikely in REM as compared to deep sleep), with the majority of coughing occurring during wakefulness. When the system detects a possible cough signature on the audio processing side, if the subject is determined to be in deep sleep or REM sleep, then the cough signature is assigned as reduced probability of in fact being a cough. Such factors can also augment the detection of a cough from another subject. For example, sound detected by a microphone or other acoustic sensor may be determined to have come from a bed partner if the monitored subject is determined to be in deep or REM sleep based on contactless sleep staging. However, if the bed partner has a spasm of coughing, this can lead to awakening of the monitored subject; in such a case, the respiratory waveform as detected via the contactless sensing may be used to verify the cough source (e.g., the monitored subject, a bed partner), using the knowledge, for instance, that an arousal followed by a cough is significantly more common than a cough during sleep followed by arousal.

As the incidence of cough increases during the night, the monitored subject's sleep score may decrease, and the system may correlate the sleep score with activity levels during the day in order to estimate whether the risk of an exercise induced event is heightened. Analysis of a reduction in sleep score due to cough (with wakefulness) or snoring, can be indicative of a worsening respiratory infection, and in turn an increased risk of the subject's condition worsening from an exercise induced event.

Environmental Signal Analysis and Processing

In addition to aggregating physiological data, the system can also optionally aggregate data from other sources, such as environmental data (e.g., allergy alert, humidity, air quality and related parameters).

Poor air quality, or combinations of temperature and humidly can be a risk factor for COPD patients with borderline oxygen desaturations (i.e., those with significant nocturnal oxyhemoglobin desaturation).

A camera (for example a built-in camera of a smart device) may be used to detect hives or eczema—such information may also be informative when considering the possibility of undiagnosed or diagnosed asthma.

Cold weather can lead to bronchoconstriction, e.g., via facial cooling. Therefore, the system may preempt bronchoconstriction by analyzing current temperature and atmospheric pressure, predicted temperatures and atmospheric pressure, and historical data. The system may then recommend that the user wear suitable clothing based on the analysis. The system may also advise the user regarding their risk levels.

Local pollution levels (airborne allergens) may be similarly used to gauge asthma risk and predict severity. Allergy alerts may also be incorporated into a decision process. For example, the system may make a determination regarding medication delivery (e.g., allergy medication, other medications for conditions worsened by allergens) based on allergen levels. Allergies may also be precursors for asthma.

In a system that polls domestic environmental monitoring systems for temperature, humidly, and air quality data from, such as sensors in a house, the polled environmental data may be monitored for extremes, such as those that might trigger an asthma or COPD exacerbation. The system may also optionally control climate control system (heating, air conditioning, ventilation systems, etc.) such as by interfacing with thermostat, HVAC control system, or other environmental control unit. Dust mites, dander and so forth in bedding may be detected using an air quality sensor, and in the case where air quality drops to an undesirable level (either predetermined or based on trend data) the system may provide an alert, such as a notice to change bed linens. The system may further determine a preferred time to provide the alert (e.g., when there is movement detected by a bedside motion sensor).

Utilizing location data from one or a multitude of users, it is possible to plot environmental data on a map. Thus, a database of location aware asthma areas, based on time and location, may be built. Such information may help a sufferer to move from an uncontrolled to controlled state.

In other words, the automatic detection of all environmental and other risk conditions may be performed; additionally, it is possible to use subject-reported information about an asthma or COPD event or exacerbation for future reference in a database, and to improve forecasting for that and possibly other sufferers.

For the case of an air quality mask active device with sensors, it is feasible to monitor respiration rate, depth and variability to detect breathing change, and optionally to deliver medication. The parameters can also be transmitted to a smart-device or monitoring center. The air quality sensor may be portable, or may be part of a PAP device with the ability to deliver medication.

Risk Analysis

As described above, the system is capable of taking an algorithmic approach to predict immediate occurrences, e.g., condition (disease) detection as it is happening or just about to happen. However, the system is also capable of carrying out more long-term predictive analysis. In other words, the system may take a forward looking approach as to where intervention can be made in order to avoid onset or worsening of the condition altogether. Thus, it is desirable that unusual behavior be flagged by the system in advance, in order that the system can act in a preventative manner (e.g., suggesting improvements before any issue is detected). For example, a "normal" person using the system could be advised that they are at risk of developing a chronic disease, and can be provided with instructions as to how to counteract such a risk.

The predictive algorithm itself may be implemented on a computing device (e.g., a PC, server, cloud service, smart-device app or variant) provided with access to a database storage device(s). The algorithm may be based on a system of rules analyzing a multitude of data sources, and may draw on historical data stored in the database. The algorithm may rely on rules and/or thresholds, which may be varied based on, for instance, adaptive probabilistic weightings. Such rules and thresholds may be based on either or both user-specific data and population-based demographic data.

The system may optionally connect to medical information systems via the Health Level Seven (HL7) standard or similar. It may also connect to telehealth systems using other interfaces, or to consumer systems using third party published APIs (Application Program Interfaces) such as commercial systems from FitBit, Apple HealthKit, Samsung S-Health, Jawbone, Basis, Misfit and so forth.

By learning a personal baseline of the user, it can be implemented to learn the user's trigger parameters (e.g., parameters representing conditions that lead to exacerbation). Feedback regarding a detected trigger, such as an alert, may be provided to a mobile or fixed device for the user's information. In some examples, the user may further contribute to the system's learning process by confirming or denying the alert. In the case of denying the alert, such end-user feedback would amount to recording a false positive detection, which may further aid future classifications and detection.

In order to conduct a multi-parameter holistic analysis of the health on an individual person, the system may further be aware of other context such that it may relate relevant data to the correct user. For example, an insurance company might provide a discount to a user of the system based on the user meeting certain health improvement targets. Such targets could be to achieve a decrease in average heart rate, decrease in breathing rate, increase in steps and exercise intensity and decrease.

The holistic analysis may use, for example, data indicative of changes in galvanic skin response and/or skin temperature recorded by a wearable sensor. Specific heart rate and GSR changes may be cross referenced with exercise intensity data to indicate whether a particular change is mediating stress event or activity. For each person, they may exhibit specific sequences of heart rate, breathing rate, and GSR changes in response to exercise or a stress event.

Longer term patterns in exercise intensity and steps taken can be correlated with user specific behaviors (e.g., to determine whether exercise is a trigger for an asthma attack, or whether an overall risk has been reduced by gradual training leading to improved cardiorespiratory patterns).

The system for managing the pattern recognition process may be capable of accepting multiple input parameters, and may optionally assume that a quality estimator has already been executed on the data in order to discard or flag any poor quality data. It is recognized that some of the input data may be dimensionally redundant, and that a process such as randomized PCA (principal component analysis) may be applied to reduce any such redundancy prior to further processing.

If a large training dataset (labelled data) is available, a supervised classification system may be employed, whereby the training dataset is provided to the system to produce model parameters. Where there is training data, but the dataset is not as large, a semi-supervised or unsupervised learning feature hierarchy (e.g., "deep learning" using neural networks) approach with techniques such as sparse coding (e.g., LCC local coordinate coding, drawn from the image processing field) or other, may be employed. Such approaches may be beneficial in cases where a particular pattern manifests in the data. Other systems such as averaged decisions trees using random forests (using a data subsets for "out of bag" (OOB) performance estimation during training) may be used for classification. Random forests are a form of nearest neighbour predictor; they can cope with unbalanced and missing data, although some care must be taken when using for regression (i.e., selecting a diverse representative training set and managing corrupted data) as they cannot predict beyond the range in the training data, and for very noisy data, may over-fit.

The system may further be capable of continually updating risk analysis of the user based on the monitored parameters.

Asthma and COPD Treatment

Inhaler Usage and Control, e.g., for Asthma

Figure 6A:
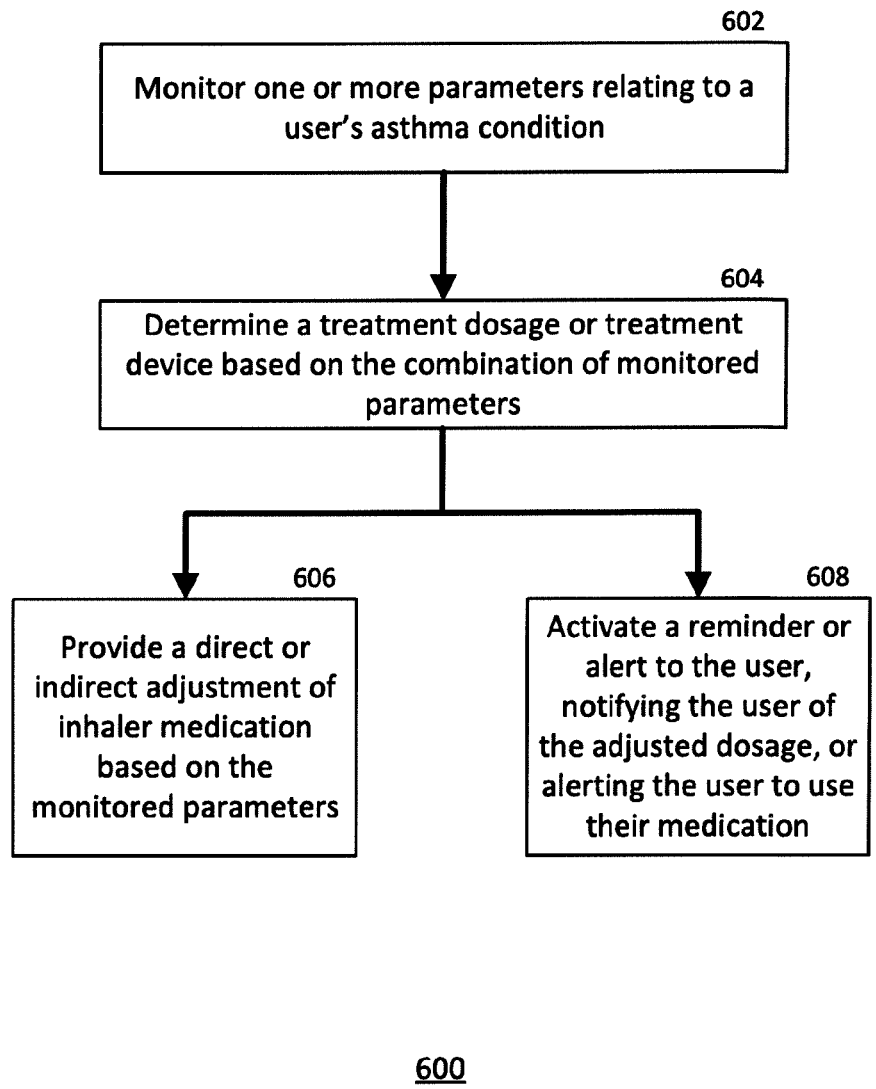
FIG. 6A illustrates example processes of a method for monitoring and managing asthma of a patient in accordance with one or more versions of the present technology described herein.

FIG. 6A provides a flow diagram of a method 600 for a person with asthma and using an inhaler to determine when or whether to use an inhaler, adjust the dosage on a metered inhaler, vary number of "puffs," or similar. At 602, one or more parameters relating to the asthma condition are monitored. For example, at least one physiological parameter and at least one environmental parameter (e.g., relating to an outdoor or indoor environment of the user) may be gathered. Parameters that may be monitored include, perceived shortness of breath/subjective breathing conditions and patterns, cardiac conditions and patterns, changes in skin temperature, blood pressure readings, airborne irritants, seasonal factors, weather conditions, and indoor climate conditions. Sleep parameters, activity levels and other lifestyle parameters may also be monitored, as well as devices such as peak flow meters.

At 604, a treatment dosage or a treatment device of the user is determined based on the combination of data gathered at 602. Any of the above example methods or processes may be employed in determining treatment dosage. In the case of an inhaler, treatment dosage may involve either of a number of puffs from the inhaler, or an amount of dosage on a metered inhaler.

At 606, a direct or indirect adjustment of inhaler medication is provided in response to the monitored parameters. Alternatively, or additionally, at 608, reminders or alerts to the user notifying the user of the adjusted dosage, or alerting the user to use their medication, may be activated and/or other lifestyle parameters may be adjusted.

COPD Monitoring

COPD is typically characterized as having low airflow on lung function tests. A person suffering from COPD may use an inhaler, nebulizer, supplemental oxygen or other measures. In this respect, the method 600 for treating asthma, above, may similarly be applied for treatment of COPD. In the case of a user using a nebulizer instead of an inhaler, the dosage determined at 604 may be an amount or concentration of medication provided by the nebulizer. Similarly, for a user treated with an oxygen supply, the concentration of oxygen provided to breathable air may constitute a dosage for purposes of this process.

Figure 6B:
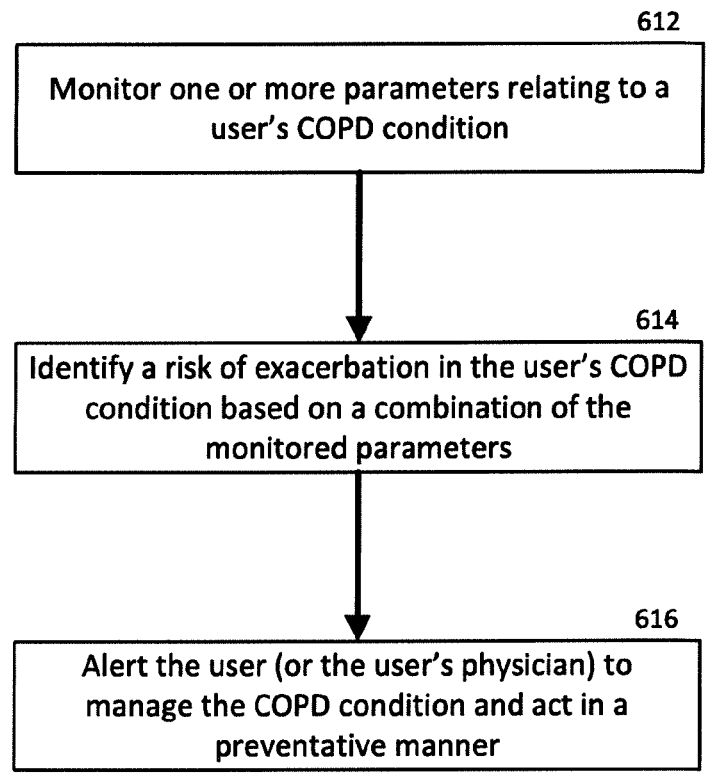
FIG. 6B illustrates example processes of a method for monitoring and managing COPD of a patient in accordance with one or more versions of the present technology described herein.

FIG. 6B provides a flow diagram of an additional method 610 for monitoring a chronic disease such as Chronic Obstructive Pulmonary Disease (COPD). At 612, one or more parameters relating to the COPD condition are tracked. The parameters may include any of the above listed parameters at 602, as well as information read from a medication or oxygen delivery system, or from tracking a chronic cough that is monitored while the user is in bed. The parameters may be collected from a specific end-user and their micro and macro environments.

At 614, the system may flag risky conditions, such as those conditions that indicate an abnormal condition (e.g., severity, or an increase in severity, of the COPD condition) based on the monitored parameters. The system may also be capable of detecting or identifying deviations from normal (healthy) signals based on a user-specific baseline, thereby predicting an adverse or abnormal condition before it occurs.

At 616, the system may alert the user and/or connect to a medical information system, to empower one or both of the user and their physician to manage the COPD condition and act in a preventative manner.

A similar process may be employed for management of congestive heart failure (CHF) or other chronic diseases.

Lifestyle Management and Prediction

Figure 6C:
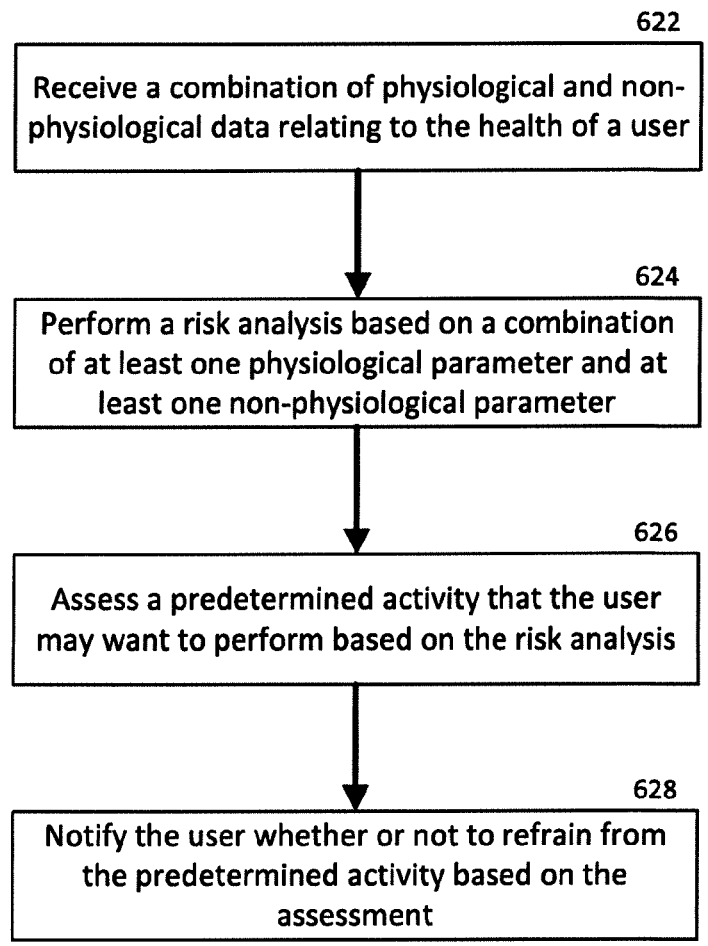
FIG. 6C illustrates example processes of a method for preventing future risk or exacerbation of a monitored chronic condition, in accordance with one or more versions of the present technology described herein.
Figure 7A:
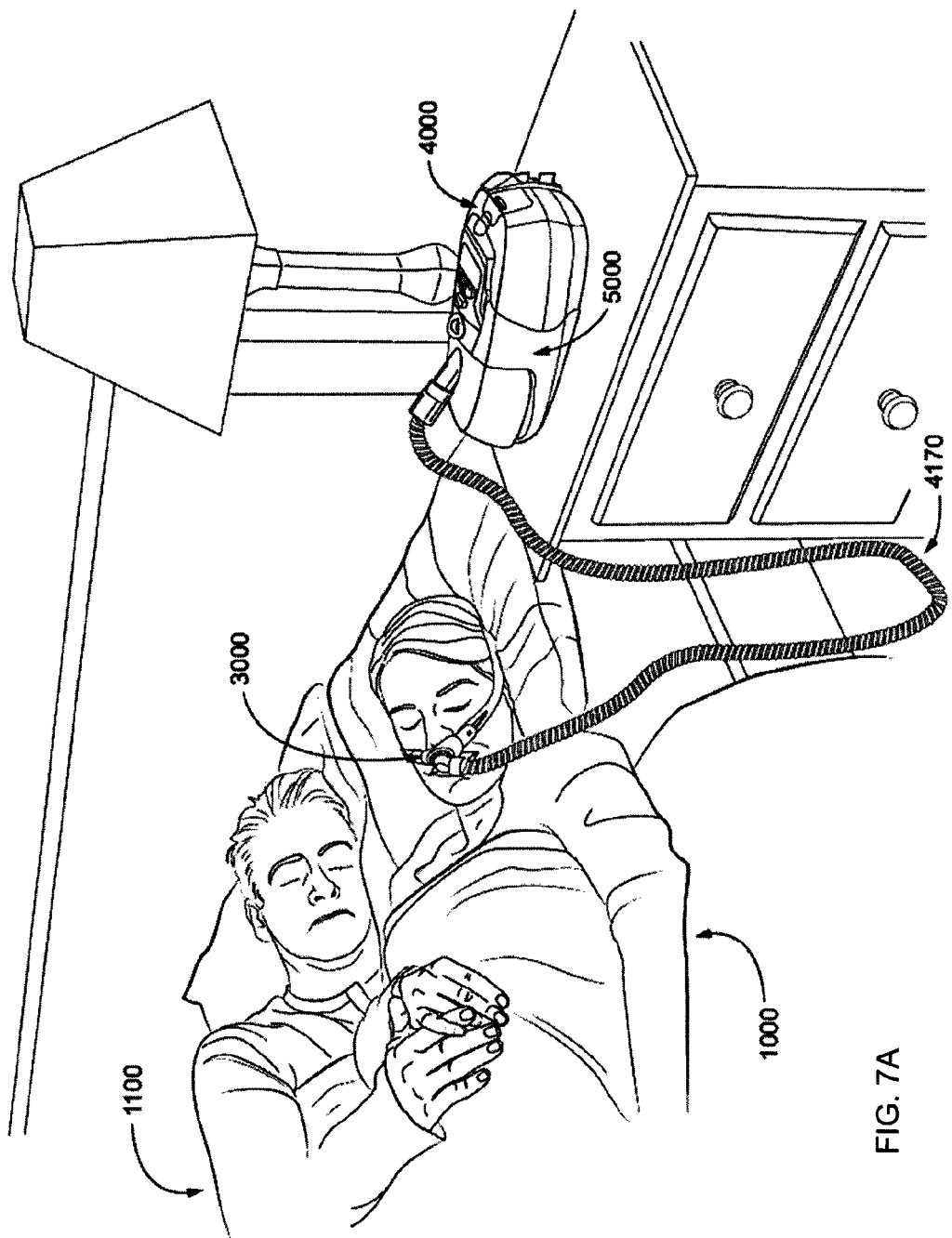
FIG. 7A shows a system in accordance with the present technology. A patient 1000 wearing a patient interface 3000 receives a supply of pressurised air from an RPT device 4000. Air from the RPT device 4000 is humidified in a humidifier 5000, and passes along an air circuit 4170 to the patient 1000. A bed partner 1100 is also shown.
Figure 7C:
FIG. 7C shows an RPT device 4000 in use on a patient 1000 with a full-face mask 3000.
Figure 8:
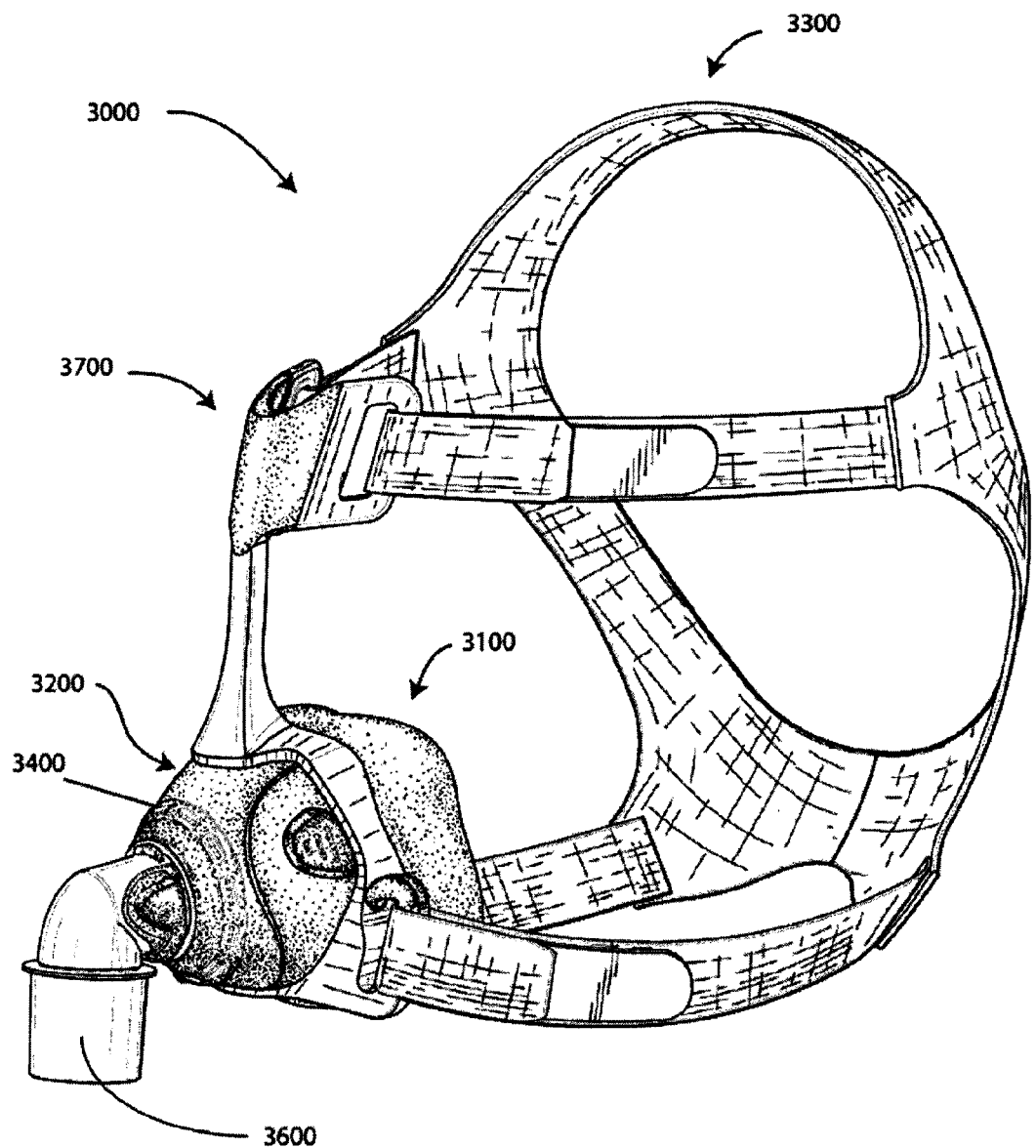
FIG. 8 shows a non-invasive patient interface 3000 in the form of a nasal mask.
Figure 9A:
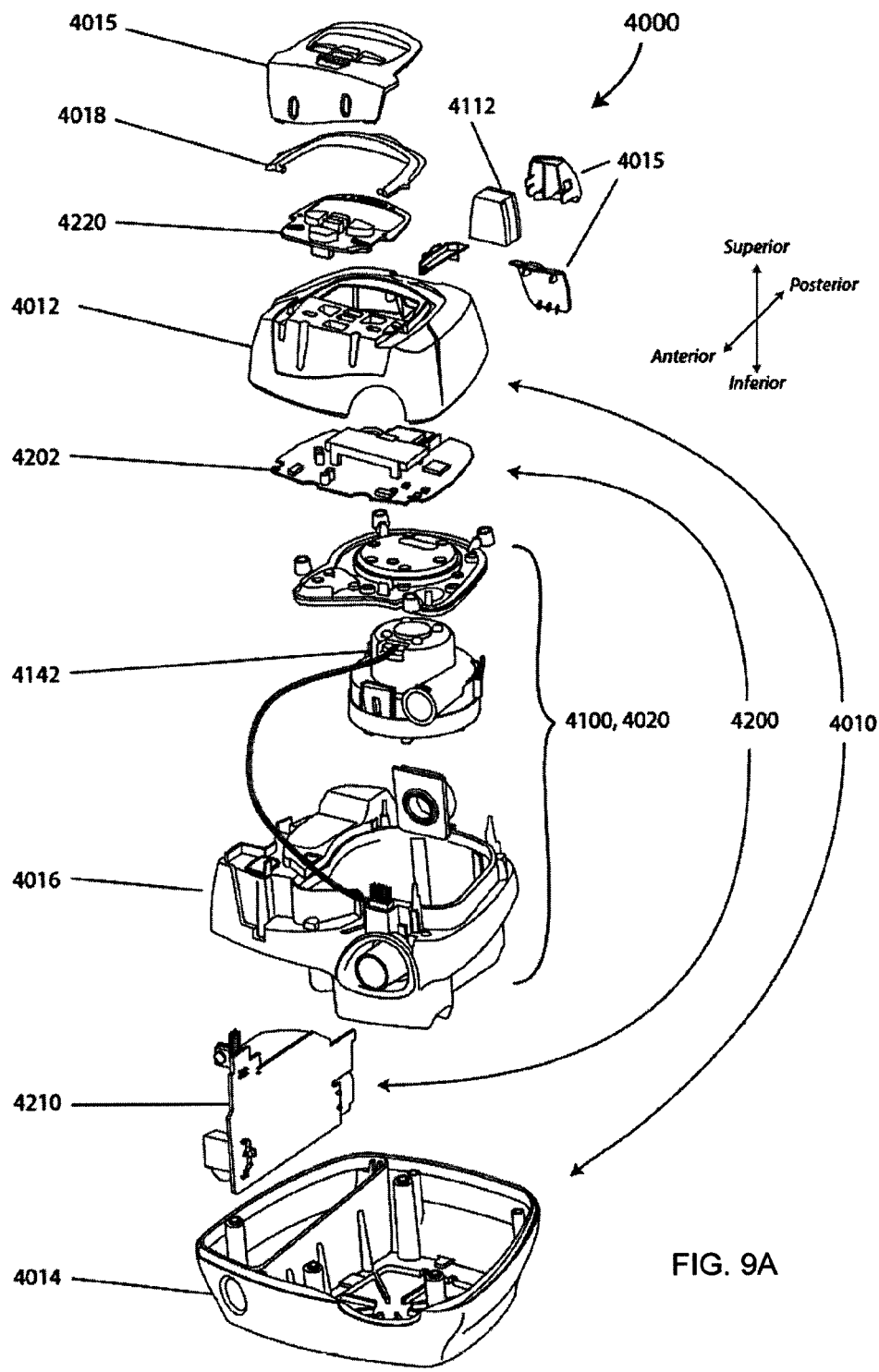
FIG. 9A shows an RPT device 4000 in accordance with one form of the present technology.
Figure 9B:
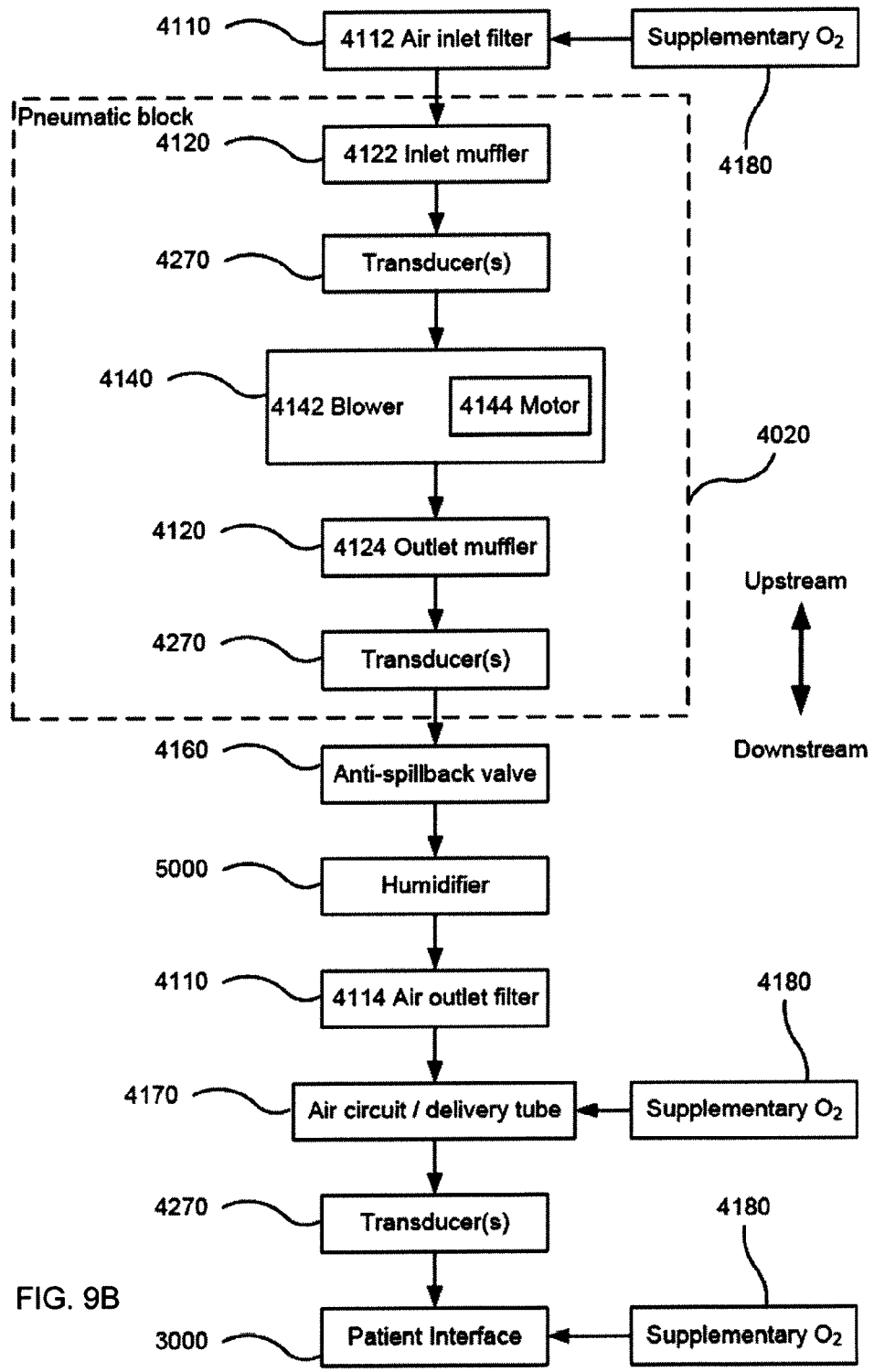
FIG. 9B shows a schematic diagram of the pneumatic circuit of an RPT device 4000 in accordance with one form of the present technology. The directions of upstream and downstream are indicated.
Figure 9C:
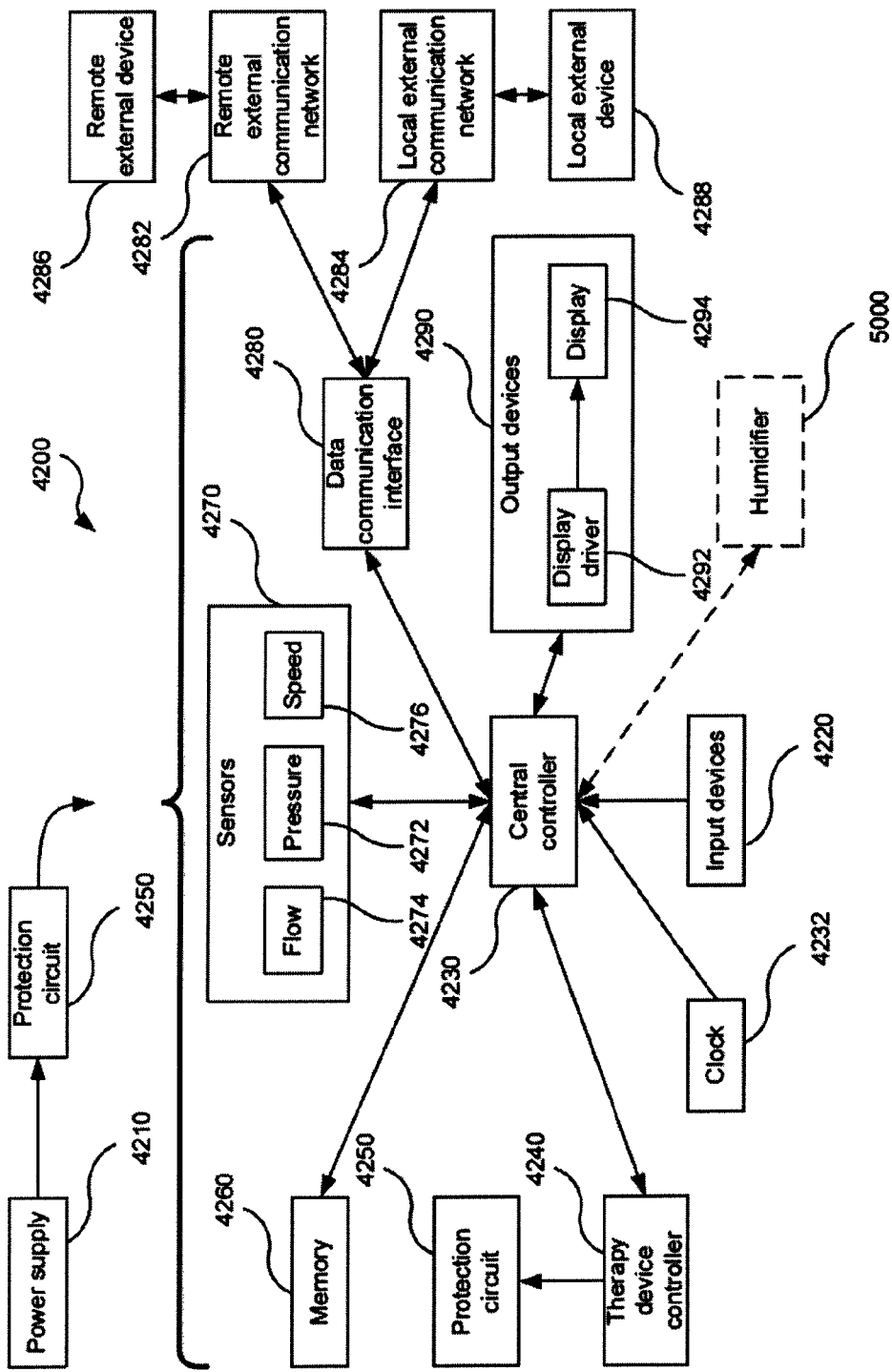
FIG. 9C shows a schematic diagram of the electrical components of an RPT device 4000 in accordance with one aspect of the present technology.
Figure 9D:
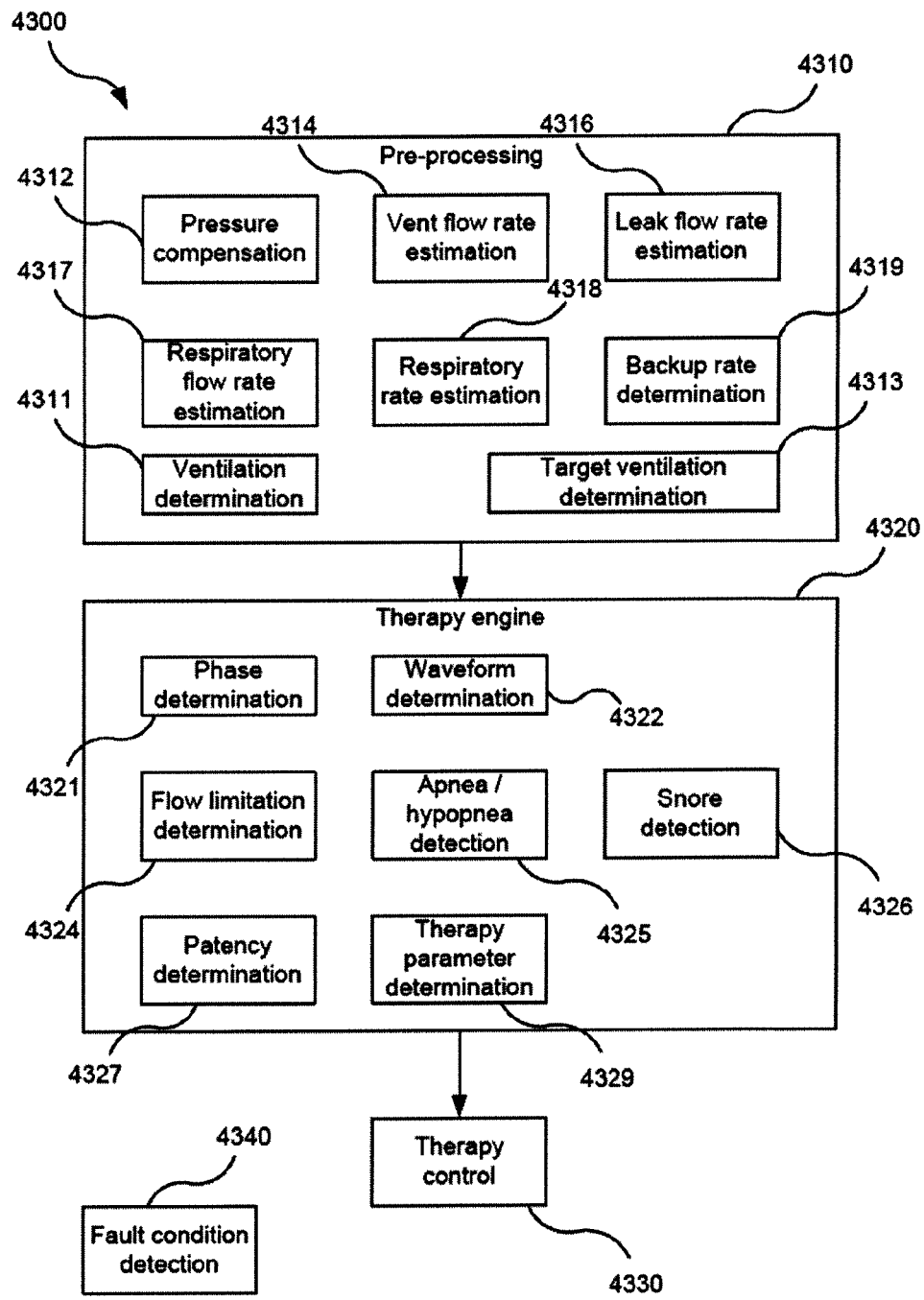
FIG. 9D shows a schematic diagram of the algorithms 4300 implemented in an RPT device 4000 in accordance with an aspect of the present technology.
Figure 9E:
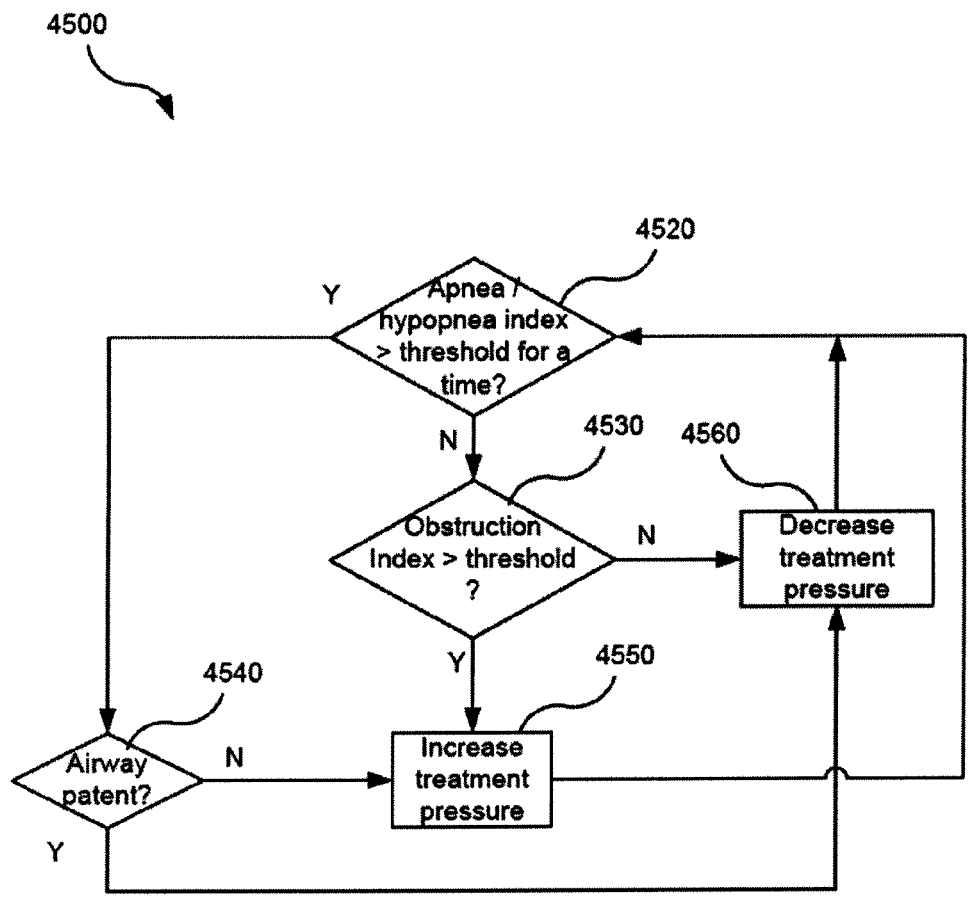
FIG. 9E is a flow chart illustrating a method 4500 carried out by the therapy engine module 4320 of FIG. 9D in accordance with one aspect of the present technology.

As explained above, lifestyle management may involve not only monitoring of existing conditions, but prediction of future conditions, as well as providing helpful information to a user (even a healthy user) to avoid onset of health problems. FIG. 6C provides a flow diagram of a method 620 for managing health of a user. At 622, the system may receive both physiological data and non-physiological data. Examples of such data have are enumerated above in connection with the methods of FIGS. 6A and 6B.

At 624, the system may perform a risk analysis based on a combination of at least one physiological parameter and at least one non-physiological parameter received at 622. In some cases, and as explained in greater detail above, training data may be input into the system in order to improve the system's learning ability, and capability to detect risks in the user's health. Also, in some cases, the system may be trained to identify anomalies in the data (such as a user falling or changing position in bed). The system may further track trends in such anomalies (increased turning during sleep), or alternatively learn to discount the data gathered from the anomaly behavior.

At 626, the system may assess a predetermined activity that the user may want to perform, such as exercising, going outdoors, or smoking. These activities may pose a health risk to the user depending on whether certain physiological and non-physiological combinations of parameters are met, such as a user being short of breath and the temperature being cold, or the user having increased frequency of coughing at night and wanting to smoke a cigarette. Assessment of such activities based on the gathered parameters may be performed using statistical models.

At 628, the system notifies the user whether or not to refrain from the predetermined activity based on the assessment from at 626. In some cases, the system may notify the user to conditionally refrain from an activity, such as not to perform the activity until after the user takes treatment for a monitored condition. For example, if the user suffers from asthma, the system may notify the user to user an inhaler before exercising. In this respect, such notification amounts to a conditional instruction (e.g., not to exercise unless medication is first taken).

Detection of asthma or other chronic diseases may be based on any one or combination of breathing features (e.g., breathing rate, inspiration to expiration time, breathing amplitude as assessed by local amplitude detection, comparison to personalised baseline measures) and heart rate features (e.g., heart rate variability, comparison to personalised baseline measures). In healthy people, the inspiration/expiration time may be roughly symmetrical. However, in subjects with respiratory disease such as COPD, inspiration/expiration time may become asymmetric, with the largest change seen in the expiration waveform. The transition from a normal baseline shape to COPD-like asymmetry is an important feature that may be used to assess the risk of an exacerbation, along with amount (duration and intensity) of activity, environmental effects (e.g., humidity, temperature, air quality, weather forecast, location), etc. In terms of strong smells and particulate levels, that information can be crowd-sourced for both internal areas (usually public spaces) and external areas. For example, industrial areas may be particularly troublesome spots in terms of air quality, and areas in which the prevailing wind direction is downstream from such sites. A user may intuitively know the "risky areas" in terms of disease condition trigger in their locality, but can gain far more benefit from the system if they travel to another area or country with which they are not familiar. In such instances, advance warnings of trouble spots in the user's destination location or along the user's projected route may be provided to the system's front end application).

In asthmatic subjects with increased respiratory sinus arrhythmia (RSA—increased vagal activation), breathing and heart parameters may be tracked in order to estimate RSA over time, and to check for changes in the parameters (as compared to, say, a baseline determined during training of the system based on prior detected events). Respiratory rate, such as large increases in respiration rate, may be tracked (e.g., for a specific person with a respiration rate of 27 breaths per minute during a respiratory attack, reducing the respiration rate to 20 breaths per minute in the hour after treatment for an event, and then further reducing to baseline of 17 breaths per minute). Changes (e.g., increases) in body temperature can indicate impending infection, and increased risk. This combined with an increase in breathing rate may be an indication of an inflammatory response (e.g., inflamed airway). The user can also indicate to the system (e.g., via a software application) if they have a runny nose.

The system determinations may feed in to dosage recommendation, or recommended adjustments to a current dosage. A recommended treatment can be provided to the user by adjusting parameters of a device in communication with the system for administering or providing medication, and/or by providing an alert to the user to prepare for a possible exacerbation in their condition. Any such activity by the system may be combined with an alert to a physician, an update to the EMR of any recommended changes in treatment, and/or a confirmation whether the change was in fact made by the subject (e.g., if 2 extra puffs of a relief inhaler were recommended when a risk condition was detected, indicating whether these puffs were actually taken using the smart inhaler or smart case). Alternatively, or in addition, an oral systemic corticosteroid may be recommended. A physician may optionally be required to accept a suggested medication change for the patient before the dosage change is recommended by the system (human intervention/safeguard). In other cases, a subject may use a nebuliser (for example at home, or in a portable form factor—and often in children or infants that have difficult using an inhaler). In an increased likelihood of a COPD exacerbation is detected, a recommendation to use (or increase the quantity of) supplemental oxygen may is made. Indeed, where supplemental oxygen is in use, the remaining gas level can be communicated via an enabled gas tank/apparatus to the relevant management entity to ensure that more gas is delivered to the tank/apparatus before the supply runs out. For the case of an oxygen concentrator, if the internal medium needs servicing or a replacement cartridge, this too can be automatically communicated to the appropriate monitoring centre/servicing company so that therapy is not interrupted.

In a bedroom environment, recommendations on suitable sleeping conditions may be made—both in terms of optimising sleep quality, as well as to reduce the risk of cough, and ultimately exacerbation. This may be done by monitoring any one or combination of air temperature, humidity, and air quality. The available parameters may be controlled automatically via a building, air handling or local humidifier and/or air conditioning/heating unit. During the day when the bedroom is empty, these systems may deliberately increase airflow and automatically open vents/blinds in order to reduce humidity and freshen the room. The system can also manage the length of time that bedclothes have been on the bed (e.g., remind the user to wash bedding weekly), as well as provide recommendations as to the temperature at which to wash them (e.g., to reduce dust mites, germs, etc.) or other recommendations (e.g., adding an extra laundry detergent at lower temperatures, or washing at 60° C. where supported by the bed clothes). The room can also be warmed up to a suitable sleeping temperature automatically when coming close to bed time. The system may also provide specific feedback advice to a user, such as to adjust humidity in the room based on measurements taken and/or local weather pattern analysis. For the bedroom environment, the target is generally about 30-50% humidity—e.g., not too dry, and not too wet (thereby reducing allergens such as mould formation). This change can be achieved via direct control of a network attached humidifier, or by directions to the user to make an adjustment to a manually controlled device. Another option is to enable the sale of a humidifier (with associated dehumidification function) via an e-commerce platform. In terms of quantifying mould and detected particulates in the sleeping environment, analysis of airborne particles/particulates, and of volatile organic compounds (VOCs) such as benzene, formaldehyde, gasoline, phenol, styrene, toluene, xylene, perchloroethylene, etc., can be performed by specialised particulate and VOC sensing.

The system also allows the gradual reduction of asthma medication as the monitored condition is brought under control, e.g., after a three month trend indicates an improvement in breathing condition. Adjusting the long term control medication may involve specific parameters for the subject being adjusted by the system (e.g., how much medication to take, when to take the medication, etc.). For example, if it is determined that a control inhaler should be taken twice a day at 12 hour intervals, the system may remind the subject to take their medication at the determined intervals to maintain their stable baseline asthma/chronic disease management.

Where an app-enabled system is used, the system can optionally inspect the subject's upcoming calendar, and note upcoming sports/exercise activities (especially where strenuous exercise is suspected of leading to large airway obstruction during or after exercise). These patterns may also be learned based on prior activity trends (e.g., to automatically detect a daily weekday gym visit, or evening dog walk). Shortly before an exercise event is scheduled to start, the system may recommend treatment to the patient (e.g., 2 or 4 puffs of a short acting beta 2-agonist). Depending on the nature of the personalised asthma condition as monitored, such inhaler use might be recommended every twenty minutes for up to an hour.

If an event (e.g., an asthma event) does occur during exercise, in a severe case, additional medication (e.g., 4 to 6 puffs of a relief inhaler) may be recommended by the system. Where the detected condition does not rapidly improve, the system can prepare and then initiate a call to the emergency services on behalf of the subject, and/or sound an audible voice confirmation or alert tone.

If a less severe event occurs that is managed by the medication, breathing exercises may be recommended and guided by the system on the user's smart device. If a smart case with any one of an inbuilt spirometer, a connected spirometer, or a spirometer with a reading that can be manually entered into an app, is available, the spirometer's peak flow reading can be analysed by the system after (and preferably before) the event in order to check for deviation from user-specific baseline values.

The system can also detect and record initial asthma trigger parameters which led to an asthma attack (sensed physiological conditions, location, and environmental/weather conditions), and can also estimate the risk of a subsequent airway obstruction (e.g., within 3 to 8 hours) after the initial exposure to these parameters, and recommend a mitigation such as inhaled steroids.

In the case that an event/exacerbation/decompensation causes a hospitalisation, the system can continue to monitor the subject, and recommend an optimised discharge plan. Updated medication settings may be read by the system from the EMR, and home, hospital, and estimated home release baseline parameters may be calculated. For example, a short term beta agonist might be used relatively infrequently (say on 1 or 2 days per week), more regularly such as 2 to 4 days per week, or regularly such as daily, or multiple times per day. Different types of inhalers, such as metered dose inhaler or dry powder inhaler, may be supported by the system. As noted, a communication-enabled inhaler may be capable of communicating both its location and its remaining capacity.

1.1 Optional Example Treatment Systems

As previously mentioned, in one form, the present technology may include an apparatus or device for treating and/or monitoring a respiratory disorder. The apparatus or device may be an RPT device 4000 for supplying pressurised air to the patient 1000 via an air circuit 4170 leading to a patient interface 3000. In the following description, the RPT device may be considered in reference to FIGS. 7-10.

1.2 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, a connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to an airway of the patient so as to facilitate the supply of pressurised air to the airway.

1.3 RPT Device

An RPT device 4000 in accordance with one aspect of the present technology comprises mechanical and pneumatic components 4100, electrical components 4200 and is programmed to execute one or more algorithms 4300. The RPT device 4000 may have an external housing 4010 formed in two parts, an upper portion 4012 and a lower portion 4014. In one form, the external housing 4010 may include one or more panel(s) 4015. The RPT device 4000 may comprise a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying pressurised air (e.g., a blower 4142), an outlet muffler 4124, and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

1.3.1 RPT Device Mechanical & Pneumatic Components

An RPT device 4000 may comprise one or more of the following components in an integral unit. In an alternative form, one or more of the following components may be located as respective separate units.

1.3.1.1 Air Filter(s)

An RPT device 4000 in accordance with one form of the present technology may include an air filter 4110, or a plurality of air filters 4110. In one form, an air inlet filter 4112 is located at the beginning of the pneumatic path upstream of a pressure generator 4140.

In one form, an air outlet filter 4114, for example an antibacterial filter, is located between an outlet of the pneumatic block 4020 and a patient interface 3000.

1.3.1.2 Muffler(s)

An RPT device 4000 in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

1.3.1.3 Pressure Generator

In one form of the present technology, a pressure generator 4140 for supplying pressurised air is a controllable blower 4142. For example, the blower 4142 may include a brushless DC motor 4144 with one or more impellers housed in a volute. The pressure generator 4140 may be capable of generating a supply or flow of air, for example at about 120 litres/minute, at a positive pressure in a range from about 4 cmH$_2$O to about 20 cmH$_2$O, or in other forms up to about 30 cmH$_2$O.

The pressure generator 4140 is under the control of the therapy device controller 4240.

In other forms, a pressure generator 4140 may be a piston-driven pump, a pressure regulator connected to a high pressure source (e.g., compressed air reservoir), or a bellows.

1.3.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 are constructed and arranged to generate data representing respective properties of the air flow, such as a flow rate, a pressure or a temperature, at that point in the pneumatic path.

In one form of the present technology, one or more transducers 4270 are located proximate to the patient interface 3000.

In one form, a signal from a transducer 4270 may be filtered, such as by low-pass, high-pass or band-pass filtering.

1.3.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

1.3.1.6 Air Circuit

An air circuit 4170 in accordance with one aspect of the present technology is a conduit or tube constructed and arranged to allow, in use, a flow of air to travel between two components such as the pneumatic block 4020 and the patient interface 3000.

1.3.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

1.3.2 RPT Device Electrical Components

1.3.2.1 Power Supply

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

1.3.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

1.3.2.3 Central Controller

In one form of the present technology, the central controller 4230 is a processor suitable to control an RPT device 4000 such as an x86 INTEL processor.

A central controller 4230 suitable to control an RPT device 4000 in accordance with another form of the present technology includes a processor based on ARM Cortex-M processor from ARM Holdings. For example, an STM32 series microcontroller from ST MICROELECTRONICS may be used.

Another central controller 4230 suitable to control an RPT device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the central controller 4230 for the RPT device 4000. For example a processor from the MSP430 family of microcontrollers, manufactured by TEXAS INSTRUMENTS, may be used.

In another form of the present technology, the central controller 4230 is a dedicated electronic circuit. In another form, the central controller 4230 is an application-specific integrated circuit (ASIC). In another form, the central controller 4230 comprises discrete electronic components.

The central controller 4230 is configured to receive input signal(s) from one or more transducers 4270, one or more input devices 4220, and the humidifier 5000.

The central controller 4230 is configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein such as the one or more algorithms 4300 expressed as computer programs stored in a non-transitory computer readable storage medium, such as memory 4260. In some forms of the present technology, as previously discussed, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

While the central controller 4230 may comprise a single controller interacting with various sensors 4270, data communications interface 4280, memory 4260, as well as other devices, the functions of controller 4230 may be distributed among more than one controller. Thus, the term "central" as used herein is not meant to limit the architecture to a single controller or processor that controls the other devices. For example, alternative architectures may include a distributed controller architecture involving more than one controller or processor. This may include, for example, a separate local (i.e., within RPT device 4000) or remotely located controller that perform some of the algorithms 4300, or even more than one local or remote memory that stores some of the algorithms. In addition, the algorithms when expressed as computer programs may comprise high level human readable code (e.g., C++, Visual Basic, other object oriented languages, etc.) or low/machine level instructions (Assembler, Verilog, etc.). Depending on the functionality of an algorithm(s), such code or instructions may be burnt in the controller, e.g., an ASIC or DSP, or be a run time executable ported to a DSP or general purpose processor that then becomes specifically programmed to perform the tasks required by the algorithm(s).

1.3.2.4 Clock

The RPT device 4000 may include a clock 4232 that is connected to the central controller 4230.

1.3.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

1.3.2.6 Protection Circuits

An RPT device 4000 in accordance with the present technology may comprise one or more protection circuits 4250.

One form of protection circuit 4250 in accordance with the present technology is an electrical protection circuit.

One form of protection circuit 4250 in accordance with the present technology is a temperature or pressure safety circuit.

1.3.2.7 Memory

In accordance with one form of the present technology the RPT device 4000 includes memory 4260, for example non-volatile memory. In some forms, memory 4260 may include battery powered static RAM. In some forms, memory 4260 may include volatile RAM.

Memory 4260 may be located on PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

1.3.2.8 Transducers

Transducers may be internal of the device 4000, or external of the RPT device 4000. External transducers may be located for example on or form part of the air delivery circuit 4170, e.g., at the patient interface 3000. External transducers may be in the form of non-contact sensors such as a Doppler radar movement sensor that transmit or transfer data to the RPT device 4000.

1.3.2.8.1 Flow Rate

A flow rate transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow rate Qt from the flow transducer 4274 is received by the central controller 4230.

1.3.2.8.2 Pressure

A pressure transducer 4272 in accordance with the present technology is located in fluid communication with the pneumatic path. An example of a suitable pressure transducer 4272 is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

1.3.2.8.3 Motor Speed

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

1.3.2.9 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g., via Ethernet, or optical fibre) or a wireless protocol (e.g., CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

1.3.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

1.3.2.10.1 Display Driver

A display driver 4292 receives as an input the characters, symbols, or images intended for display on the display 4294, and converts them to commands that cause the display 4294 to display those characters, symbols, or images.

1.3.2.10.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

1.3.3 RPT Device Algorithms

1.3.3.1 Pre-Processing Module

A pre-processing module 4310 in accordance with the present technology receives, as an input, raw data from a transducer 4270, for example a flow rate sensor 4274 or a pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, respiratory flow rate estimation 4317, ventilation determination 4311, target ventilation determination 4313, respiratory rate estimation 4318, and backup rate determination 4319.

1.3.3.1.1 Pressure Compensation

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

1.3.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

1.3.3.1.3 Leak Flow Rate Estimation

In one form of the present technology, a leak flow rate estimation algorithm 4316 receives as an input a total flow rate Qt and a vent flow rate Qv, and estimates a leak flow rate Ql. In one form, the leak flow rate estimation algorithm 4316 estimates the leak flow rate Ql by calculating an average of the difference between the total flow rate and the vent flow rate Qv over a period sufficiently long to include several breathing cycles, e.g., about 10 seconds.

In one form, the leak flow estimation algorithm 4316 receives as an input a total flow rate Qt, a vent flow rate Qv, and an estimated pressure, Pm, in the patient interface 3000, and estimates a leak flow rate Ql by calculating a leak conductance, and determining a leak flow rate Ql to be a function of leak conductance and the pressure Pm. Leak conductance may be calculated as the quotient of low-pass filtered non-vent flow rate equal to the difference between total flow rate Qt and vent flow rate Qv, and low-pass filtered square root of pressure Pm, where the low-pass filter time constant has a value sufficiently long to include several breathing cycles, e.g., about 10 seconds. The leak flow rate Ql may be estimated as the product of leak conductance and a function of pressure, Pm.

1.3.3.1.4 Respiratory Flow Rate Estimation

In one form of the present technology, a respiratory flow rate estimation algorithm 4317 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate QL from the total flow rate Qt.

In other forms of the present technology, the respiratory flow estimation algorithm 4317 provides a value that acts as a proxy for the respiratory flow rate Qr. Possible proxies for respiratory flow rate include:

Respiratory movement of the chest of the patient 1000
Current drawn by the pressure generator 4140
Motor speed of the pressure generator 4140
Trans-thoracic impedance of the patient 1000

The respiratory flow rate proxy value may be provided by a transducer 4270 in the RPT device 4000, e.g., the motor speed sensor 4276, or a sensor external to the RPT device 4000, such a respiratory movement sensor or a trans-thoracic impedance sensor.

1.3.3.1.5 Ventilation Determination

In one form of the present technology, a ventilation determination algorithm 4311 receives an input a respiratory flow rate Qr, and determines a measure Vent indicative of current patient ventilation.

In some implementations, the ventilation determination algorithm 4311 determines a measure of ventilation Vent that is an estimate of actual patient ventilation.

In one such implementation, the measure of ventilation Vent is half the absolute value of respiratory flow, Qr, optionally filtered by low-pass filter such as a second order Bessel low-pass filter with a corner frequency of 0.11 Hz.

In one such implementation, the measure of ventilation Vent is an estimate of gross alveolar ventilation (i.e. non-anatomical-deadspace ventilation). This requires an estimate of anatomical deadspace. One can use the patient's height (or arm-span in cases of severe skeletal deformity) as a good predictor of anatomical deadspace. Gross alveolar ventilation is then equal to a measure of actual patient ventilation, e.g., determined as above, less the product of the estimated anatomical deadspace and the estimated spontaneous respiratory rate Rs.

In other implementations, the ventilation determination algorithm 4311 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where $0<K<1$. There is an arbitrarily large number of measures that are exactly proportional to ventilation if the flow rate waveform shape is constant.

In other forms, the ventilation determination algorithm 4311 determines a measure Vent of ventilation that is not based on respiratory flow rate Qr, but is a proxy for the current patient ventilation, such as oxygen saturation ($SaO_2$), or partial pressure of carbon dioxide ($PCO_2$), obtained from suitable sensors attached to the patient 1000.

1.3.3.1.6 Target Ventilation Determination

In one form of the present technology, a central controller 4230 takes as input the measure of current ventilation, Vent, and executes one or more target ventilation determination algorithms 4313 for the determination of a target value Vtgt for the measure of ventilation.

In some forms of the present technology, there is no target ventilation determination algorithm 4313, and the target ventilation Vtgt is predetermined, for example by hard-coding during configuration of the RPT device 4000 or by manual entry through the input device 4220.

In other forms of the present technology, such as adaptive servo-ventilation (ASV) therapy (described below), the target ventilation determination algorithm 4313 computes the target ventilation Vtgt from a value Vtyp indicative of the typical recent ventilation of the patient 1000.

In some forms of adaptive servo-ventilation therapy, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation therapy, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4313, the recent history is of the order of several minutes, but in any case should be longer than the timescale of Cheyne-Stokes waxing and waning cycles. The target ventilation determination algorithm 4313 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

1.3.3.1.7 Respiratory Rate Estimation

In one form of the present technology, a respiratory rate estimation algorithm 4318 receives as an input a respiratory flow rate, Qr, to the patient 1000, and produces an estimate of the spontaneous respiratory rate Rs of the patient.

The respiratory rate estimation algorithm 4318 may estimate the spontaneous respiratory rate Rs over periods when the patient 1000 is breathing spontaneously, i.e., when the RPT device 4000 is not delivering "backup breaths" (described below). In some forms of the present technology, the respiratory rate estimation algorithm 4318 estimates the respiratory rate over periods when servo-assistance (defined as pressure support minus minimum pressure support) is low, in one implementation less than 4 $cmH_2O$, as such periods are more likely to reflect spontaneous respiratory effort.

In some forms of the present technology, the respiratory rate estimation algorithm 4318 estimates the respiratory rate over periods of asleep breathing, since the respiratory rate during these periods may be substantially different from the respiratory rate during wake. Anxiety typically results in a higher respiratory rate than that prevailing during sleep. When patients focus on their own breathing process, their respiratory rates are typically lower than those during normal wakefulness or during sleep. Techniques such as described in Patent Application no. PCT/AU2010/000894, published as WO 2011/006199, the entire disclosure of which is hereby incorporated herein by reference, may be used to identify periods of awake breathing from the respiratory flow rate, Qr.

In some forms of the present technology, the respiratory rate estimation algorithm 4318 estimates the spontaneous respiratory rate Rs as the reciprocal of one of a variety of well-known statistical measures of central tendency of breath duration Ttot during the period of interest. In such measures it is desirable to reject, or at least be robust to, outliers. One such measure, trimmed mean, in which the lower and upper K proportions of the sorted breath durations are discarded and the mean calculated on the remaining breath durations, is robust to outliers. For example, when K is 0.25, this amounts to discarding the upper and lower quartiles of breath duration Ttot. The median is another robust measure of central tendency, though this can occasionally give unsatisfactory results when the distribution is strongly bimodal. A simple mean may also be employed as a measure of central tendency, though it is sensitive to outliers. An initial interval filtering stage, in which contiguous time intervals corresponding to implausible respiratory rates (e.g., greater than 45 breaths/minute or less than 6 breaths/minute) are excluded as outliers from the mean calculation, may be employed. Other filtering mechanisms which may be used alone or in combination with interval filtering are to exclude any breaths that are not part of a sequence of N successive spontaneous breaths, where N is some small integer (e.g., 3), and to exclude the early and late breaths of a sequence of successive spontaneous breaths, e.g., to exclude the first and last breaths of a sequence of four breaths. The rationale for the latter mechanism is that the first and the last breaths in particular, and the early and late breaths in general, of a sequence of spontaneous breaths may be atypical; for example, the first spontaneous breath may occur as a result of an arousal, and the last spontaneous breath may be longer because of the decreasing respiratory drive which results in the backup breath which ends the sequence of spontaneous breaths.

In some forms of the present technology, the respiratory rate estimation algorithm 4318 makes an initial estimate of the spontaneous respiratory rate Rs using an initial period of estimation, to enable the subsequent processing in the therapy engine module 4320 to begin, and then continuously updates the estimate of the spontaneous respiratory rate Rs using a period of estimation that is longer than the initial period of estimation, to improve statistical robustness. For example, the initial period of estimation may be 20 minutes of suitable spontaneous breaths, but the period of estimation may then progressively increase up to some maximum duration, for example 8 hours. Rather than a rolling window of this duration being used for this estimation, low-pass filters on breath duration may be used, with progressively longer response times (more precisely, progressively lower corner frequencies) as the session proceeds.

In some forms, a suitably processed short-term (e.g., 10-minute) measure of central tendency, such as trimmed mean, may be input to a suitable low-pass filter to give an estimate Rs which changes on the time scale of hours or longer. This has the advantage that potentially large amounts of breath duration data do not need to be stored and processed, as might occur if a trimmed mean needs to be calculated on a moving window of breath duration data lasting hours or days.

In some forms of the present technology, respiratory rates measured over short periods of time, and in particular over one breath, may also be used instead of breath duration in the above-described measures of central tendency, giving generally similar but not identical results.

1.3.3.1.8 Backup Rate Determination

In one form of the present technology, a backup rate determination algorithm 4319 receives as input a spontaneous respiratory rate estimate Rs provided by the respiratory rate estimation algorithm 4318 and returns a "backup rate" Rb. The backup rate Rb is the rate at which the RPT device 4000 will deliver backup breaths, i.e., continue to provide ventilatory support, to a patient 1000 in the absence of significant spontaneous respiratory effort.

In one form of the pre-processing module 4310, there is no backup rate determination algorithm 4319, and the backup rate Rb is instead provided manually to the RPT device 4000, e.g., via the input device 4220, or hard-coded at the time of configuration of the RPT device 4000.

In one form, known as adaptive backup rate, the backup rate determination algorithm 4319 determines the backup rate Rb as a function of the spontaneous respiratory rate Rs. In one implementation, the function determines the backup rate Rb as the spontaneous respiratory rate Rs minus a constant such as 2 breaths per minute. In another implementation, the function determines the backup rate Rb as the spontaneous respiratory rate Rs multiplied by a constant that is slightly less than unity.

In one form, known as variable backup rate, the backup rate determination algorithm 4319 determines the backup rate Rb as a function of time. The backup rate Rb is initialised to a value known as the spontaneous backup rate (SBR) that is some fraction of a final target backup rate, known as the sustained timed backup rate (STBR). The fraction may be two thirds, or three quarters, or other positive values less than one. The SBR is the reciprocal of the timeout period to a backup breath when the most recent inspiration was a spontaneous (i.e., patent-triggered) breath. The STBR may be predetermined (e.g., by manual entry or hard-coding as described above) or set to some typical respiratory rate such as 15 bpm. Over time elapsed since the previous spontaneous breath, the backup rate Rb is increased from the SBR towards the STBR. The increase may be according to a predetermined profile, such as a series of steps, or a continuous linear profile. The profile is chosen such that the backup rate Rb reaches the STBR after a predetermined interval. The interval may be measured in units of time, such as 30 seconds, or relative to the patient's respiration, such as 5 breaths.

In some forms of variable backup rate, the predetermined interval over which the backup rate Rb increases from the SBR towards the STBR may be a function of the adequacy of current ventilation. In one implementation, suitable for servo-ventilation in which a target value Vtgt exists for the measure of ventilation, the backup rate approaches the STBR faster to the extent that current measure of ventilation Vent is less than the target ventilation Vtgt.

In one form of variable backup rate, known as adaptive variable backup rate, the backup rate determination algorithm 4319 determines the backup rate Rb as a function of the current estimated spontaneous respiratory rate Rs provided by the respiratory rate estimation algorithm 4318, as well as a function of time. As in variable backup rate determination, adaptive variable backup rate determination increases the backup rate Rb from the SBR towards the STBR over a predetermined interval that may be a function of the adequacy of current ventilation. The STBR may be initialised to a standard respiratory rate, such as 15 bpm. Once a reliable estimate of spontaneous respiratory rate Rs is available from the respiratory rate estimation algorithm 4318, the STBR may be set to the current estimated spontaneous respiratory rate Rs multiplied by some constant. The SBR may be set to some fraction of the STBR, as in variable backup rate. In one form, the fraction, for example two thirds, can be set to a lower value, such as 0.55, during the initial period of estimation of the spontaneous respiratory rate Rs, to accommodate occasional long breath durations in patients with relatively low respiratory rates, such as 12 breaths per minute.

In some forms, the constant by which the current estimated spontaneous respiratory rate Rs is multiplied to obtain the STBR may be slightly higher than 1, e.g., 1.1, to provide more aggressive ventilation during apneas, which may be desirable in short apneas. The constant may be somewhat lower than 1, e.g., 0.8, particularly if difficulty in resynchronisation with the patient on the return of patient effort turns out to be a problem in a particular patient. Lower backup rates make resynchronisation easier, by lengthening the expiratory pause, during which resynchronisation commonly occurs.

1.3.3.2 Therapy Engine Module

In one form of the present technology, a therapy engine module 4320 receives as inputs one or more of a pressure, Pm, in a patient interface 3000, a respiratory flow rate of air to a patient, Qr, and an estimate Rs of the spontaneous respiratory rate, and provides as an output one or more therapy parameters. In various forms, the therapy engine module 4320 comprises one or more of the following algorithms: phase determination 4321, waveform determination 4322, inspiratory flow limitation determination 4324, apnea/hypopnea determination 4325, snore detection 4326, airway patency determination 4327, and therapy parameter determination 4329.

1.3.3.2.1 Phase Determination

In one form of the present technology, a phase determination algorithm 4321 receives as an input a signal indicative of respiratory flow, Qr, and provides as an output a phase □ of a current breathing cycle of a patient 1000.

In some forms, known as discrete phase determination, the phase output F is a discrete variable. One implementation of discrete phase determination provides a bi-valued phase output F with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output F is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output F with a value of one of inhalation, mid-inspiratory pause, and exhalation.

In other forms, known as continuous phase determination, the phase output F is a continuous value, for example varying from 0 to 1 revolutions, or 0 to 2□ radians. RPT devices 4000 that perform continuous phase determination may trigger and cycle when the continuous phase reaches 0 and 0.5 revolutions, respectively. In one implementation of continuous phase determination, a continuous value of phase F is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's respiratory rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inhalation time Ti and the exhalation time Te are first estimated from the respiratory flow rate Qr. The phase □ is then determined as the half the proportion of the inhalation time Ti that has elapsed since the previous trigger instant, or 0.5 revolutions plus half the proportion of the exhalation time Te that has elapsed since the previous cycle instant (whichever was more recent).

In some forms of the present technology, suitable for pressure support ventilation therapy (described below), the phase determination algorithm 4321 is configured to trigger even when the respiratory flow rate Qr is insignificant, such as during an apnea. As a result, the RPT device 4000 delivers "backup breaths" in the absence of spontaneous respiratory effort from the patient 1000. For such forms, known as spontaneous/timed (S/T) modes, the phase determination algorithm 4321 may make use of the backup rate Rb provided by the backup rate determination algorithm 4319.

A phase determination algorithm 4321 that uses "fuzzy phase" may implement S/T mode using the backup rate Rb by including a "momentum" rule in the fuzzy phase rules. The effect of the momentum rule is to carry the continuous phase forward from exhalation to inhalation at the backup rate Rb if there are no features of respiratory flow rate Qr that would otherwise carry the continuous phase forward through the other rules. In one implementation, the more it is true that the measure of ventilation Vent (described below) is well below a target value Vtgt for ventilation (also described below), the more highly the momentum rule is weighted in the combination. However, as a result of the rapid increase in pressure support in response to mild to moderate hypoventilation (with respect to the target ventilation), the ventilation may be quite close to the target ventilation. It is desirable that the momentum rule is given a low weighting when the ventilation is close to target, to allow the patient to breathe at rates significantly lower than the respiratory rate at other times (when the patient is not in a central apnea) without being unnecessarily pushed to breathe at a higher rate by the ventilator. However, when the momentum rule is given a low weighting when ventilation is above a value which is below but close to the target ventilation, adequate ventilation may easily be achieved at a relatively high pressure support at a rate well below the backup rate. It would be desirable for the backup breaths to be delivered at a higher rate, because this would enable the target ventilation to be delivered at a lower pressure support. This is desirable for a number of reasons, a key one of which is to diminish mask leak.

To summarise, in a fuzzy phase determination algorithm 4321 that implements S/T mode, there is a dilemma in choosing the weighting for the momentum rule incorporating the backup rate Rb: if it is too high, the patient may feel "pushed along" by the backup rate. If it is too low, the pressure support may be excessive. Hence it is desirable to provide methods of implementing S/T mode which do not rely on the momentum rule described above.

A phase determination algorithm 4321 (either discrete, or continuous without a momentum rule) may implement S/T mode using the backup rate Rb in a manner known as timed backup. Timed backup may be implemented as follows: the phase determination algorithm 4321 attempts to detect the start of inhalation due to spontaneous respiratory effort, for example by monitoring the respiratory flow rate Qr as described above. If the start of inhalation due to spontaneous respiratory effort is not detected within a period of time after the last trigger instant whose duration is equal to the reciprocal of the backup rate Rb (an interval known as the backup timing threshold), the phase determination algorithm 4321 sets the phase output $\Phi$ to a value of inhalation (thereby triggering the RPT device 4000). Once the RPT device 4000 is triggered, and a backup breath begins to be delivered, the phase determination algorithm 4321 attempts to detect the start of spontaneous exhalation, for example by monitoring the respiratory flow rate Qr, upon which the phase output $\Phi$ is set to a value of exhalation (thereby cycling the RPT device 4000).

If the backup rate Rb is increased over time from the SBR to the STBR, as in a variable backup rate system described above, the backup timing threshold starts out longer and gradually becomes shorter. That is, the RPT device 4000 starts out less vigilant and gradually becomes more vigilant to lack of spontaneous respiratory effort as more backup breaths are delivered. Such an RPT device 4000 is less likely to make a patient feel "pushed along" if they would prefer to breathe at a lower than standard rate, while still delivering backup breaths when they are needed.

If the STBR in a variable backup rate system adapts to the patient's estimated spontaneous respiratory rate Rs, as in an adaptive variable backup rate system described above, the backup breaths will be delivered at a rate that adapts to the patient's own recent spontaneous respiratory efforts.

1.3.3.2.2 Waveform Determination

In one form of the present technology, the therapy control module 4330 controls a pressure generator 4140 to provide a treatment pressure Pt that varies as a function of phase $\Phi$ of a breathing cycle of a patient according to a waveform template $\Pi$ ($\Phi$).

In one form of the present technology, a waveform determination algorithm 4322 provides a waveform template $\Pi$ ($\Phi$) with values in the range [0, 1] on the domain of phase values Q provided by the phase determination algorithm 4321 to be used by the therapy parameter determination algorithm 4329.

In one form, suitable for either discrete or continuously-valued phase, the waveform template $\Pi$ ($\Phi$) is a square-wave template, having a value of 1 for values of phase up to and including 0.5 revolutions, and a value of 0 for values of phase above 0.5 revolutions. In one form, suitable for continuously-valued phase, the waveform template $\Pi$ ($\Phi$) comprises two smoothly curved portions, namely a smoothly curved (e.g., raised cosine) rise from 0 to 1 for values of phase up to 0.5 revolutions, and a smoothly curved (e.g., exponential) decay from 1 to 0 for values of phase above 0.5 revolutions. One example of such a "smooth and comfortable" waveform template is the "shark fin" waveform template, in which the rise is a raised cosine, and the smooth decay is quasi-exponential (so that the limit of $\Pi$ as $\Phi$ approaches one revolution is precisely zero).

In some forms of the present technology, the waveform determination algorithm 4322 selects a waveform template $\Pi$ ($\Phi$) from a library of waveform templates, dependent on a setting of the RPT device 4000. Each waveform template $\Pi$ ($\Phi$) in the library may be provided as a lookup table of values $\Pi$ against phase values $\Phi$. In other forms, the waveform determination algorithm 4322 computes a waveform template $\Pi$ ($\Phi$) "on the fly" using a predetermined functional form, possibly parametrised by one or more parameters (e.g., time constant of an exponentially curved portion). The parameters of the functional form may be predetermined or dependent on a current state of the patient 1000.

In some forms of the present technology, suitable for discrete bi-valued phase of either inhalation ($\Phi$=0 revolutions) or exhalation (F=0.5 revolutions), the waveform determination algorithm 4322 computes a waveform template $\Pi$ "on the fly" as a function of both discrete phase F and time t measured since the most recent trigger instant (transition from exhalation to inhalation). In one such form, the waveform determination algorithm 4322 computes the waveform template P(F, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\emptyset_e(t)$ are inspiratory and expiratory portions of the waveform template $\Pi(\angle, t)$, and Ti is the inhalation time. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

1.3.3.2.3 Determination of Inspiratory Flow Limitation

In one form of the present technology, a processor executes one or more algorithms 4324 for the detection of inspiratory flow limitation (partial obstruction).

In one form the algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified based on the phase F estimated at each instant. For example, the inspiratory portion of the breath is the values of respiratory flow for which the phase F is less than or equal to 0.5. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by central controller 4230 for the preceding several inspiratory events. This is repeated over the same inspiratory events for the second such point, and so on. Thus, for example, sixty five scaled data points are generated by central controller 4230, and represent a moving average of the preceding several inspiratory events, e.g., three events. The moving average of continuously updated values of the (e.g., sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g., thirty-two) scaled flow points to the mean overall (e.g., sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g., thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

1.3.3.2.4 Determination of Apneas and Hypopneas

In one form of the present technology, a central controller 4230 executes one or more algorithms 4325 for the detection of apneas and/or hypopneas.

In one form, the one or more apnea/hypopnea detection algorithms 4325 receive as an input a respiratory flow rate Qr and provide as an output a flag that indicates that an apnea or a hypopnea has been detected.

In one form, an apnea will be said to have been detected when a function of respiratory flow rate Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow rate Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

1.3.3.2.5 Detection of Snore

In one form of the present technology, a central controller 4230 executes one or more snore detection algorithms 4326 for the detection of snore.

In one form, the snore detection algorithm 4326 receives as an input a respiratory flow rate signal Qr and provides as an output a metric of the extent to which snoring is present.

The snore detection algorithm 4326 may comprise a step of determining the intensity of the flow rate signal in the range of 30-300 Hz. The snore detection algorithm 4326 may further comprises a step of filtering the respiratory flow rate signal Qr to reduce background noise, e.g., the sound of airflow in the system from the blower 4142.

1.3.3.2.6 Determination of Airway Patency

In one form of the present technology, a central controller 4230 executes one or more algorithms 4327 for the determination of airway patency.

In one form, airway patency algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow rate signal Qr, and determines the presence or absence of a cardiogenic signal. The absence of a cardiogenic signal is taken to be an indication of a closed airway.

1.3.3.2.7 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi) + P_0 \quad (1)$$

where:
 A is an amplitude,
 $\Phi$ is the current value of phase;
 $\Pi(\Phi)$ is the waveform template value (in the range 0 to 1) at the current value of phase, and
 $P_0$ is a base pressure.

If the waveform determination algorithm 4322 provides the waveform template $\Pi(\Phi)$ as a lookup table of values indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen pressure therapy mode in the manner described below.

1.3.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of gas whose mask pressure Pm at the patient interface 3000 is equal to the treatment pressure Pt.

1.3.3.4 Detection of Fault Conditions

In one form of the present technology, a processor executes one or more methods 4340 for the detection of fault conditions. The fault conditions detected by the one or more methods may include at least one of the following:

Power failure (no power, or insufficient power)
Transducer fault detection
Failure to detect the presence of a component
Operating parameters outside recommended ranges (e.g., pressure, flow, temperature, PaO$_2$)
Failure of a test alarm to generate a detectable alarm signal.

Figure 10:
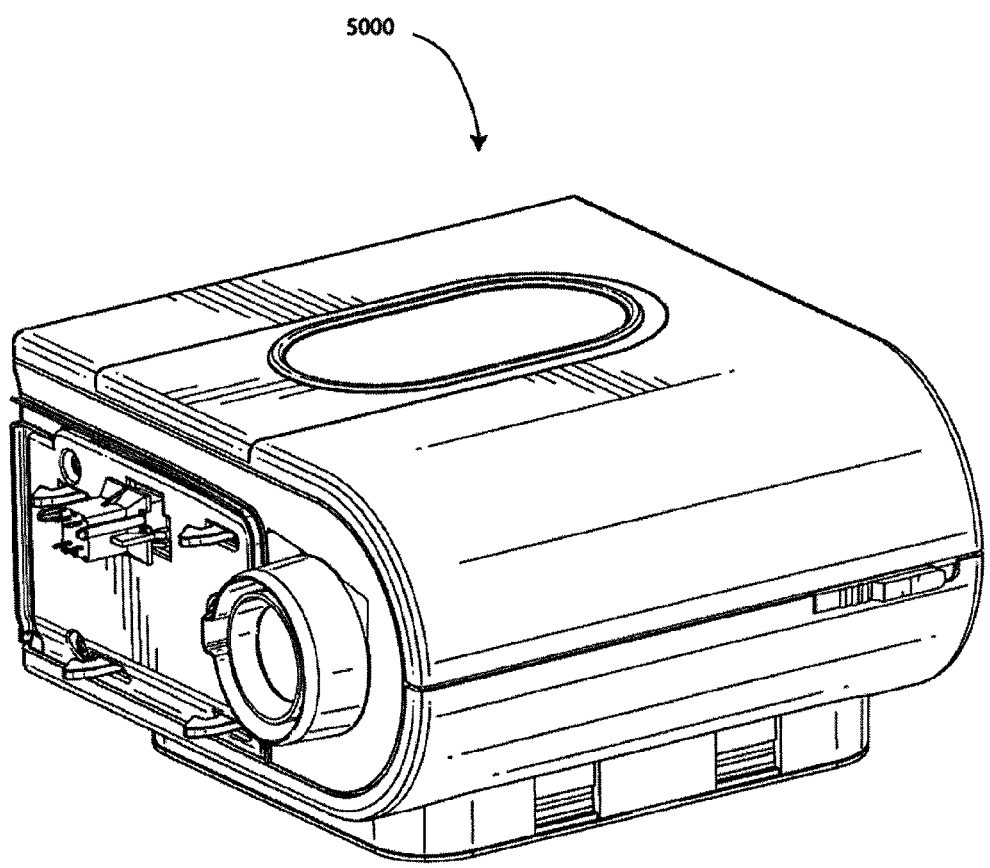
FIG. 10 shows a humidifier 5000.

Upon detection of the fault condition, the corresponding algorithm signals the presence of the fault by one or more of the following:

Initiation of an audible, visual &/or kinetic (e.g., vibrating) alarm
Sending a message to an external device
Logging of the incident 1.4 Humidifier In one form of the present technology there is provided a humidifier 5000 (e.g., as shown in FIG. 10) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

1.5 Glossary

For the purposes of the present disclosure, in certain forms of the present technology, one or more of the following definitions may apply. In other forms of the present technology, alternative definitions may apply.

1.5.1 General

Air: In certain forms of the present technology, air may be taken to mean atmospheric air, and in other forms of the present technology air may be taken to mean some other combination of breathable gases, e.g., atmospheric air enriched with oxygen.

Respiratory Pressure Therapy (RPT): The delivery of a supply of air to the airways at a treatment pressure that is typically positive with respect to atmosphere.

Continuous Positive Airway Pressure (CPAP) therapy: Respiratory pressure therapy in which the treatment pressure is approximately constant through a breathing cycle of a patient. In some forms, the pressure at the entrance to the airways will be slightly higher during exhalation, and slightly lower during inhalation. In some forms, the pressure will vary between different breathing cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

1.5.2 Aspects of the Breathing Cycle

Apnea: According to some definitions, an apnea is said to have occurred when respiratory flow rate falls below a predetermined threshold for a duration, e.g., 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate, or respiratory rate (Rs): The rate of spontaneous respiration of a patient, usually measured in breaths per minute.

Duty cycle: The ratio of inhalation time, Ti to total breath duration, Ttot.

Effort (breathing): The work done by a spontaneously breathing person attempting to breathe.

Expiratory portion of a breathing cycle: The period from the start of expiratory flow to the start of inspiratory flow.

Flow limitation: The state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: A reduction in flow, but not a cessation of flow. In one form, a hypopnea may be said to have occurred when there is a reduction in flow below a threshold for a duration. In one form in adults, the following either of the following may be regarded as being hypopneas:

a 30% reduction in patient breathing for at least 10 seconds plus an associated 4% desaturation; or
a reduction in patient breathing (but less than 50%) for at least 10 seconds, with an associated desaturation of at least 3% or an arousal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow rate (Qpeak): The maximum value of flow during the inspiratory portion of the respiratory flow rate waveform.

Respiratory flow airflow rate, patient flow airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

Inhalation Time (Ti): The duration of the inspiratory portion of the respiratory flow rate waveform.

Exhalation Time (Te): The duration of the expiratory portion of the respiratory flow rate waveform.

(total) Time, or breath duration (Ttot): The total duration between the start of the inspiratory portion of one respiratory flow rate waveform and the start of the inspiratory portion of the following respiratory flow rate waveform.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

1.5.3 RPT Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow rate will be given the symbol Q. 'Flow rate' is sometimes shortened to simply 'flow'. Total flow rate, Qt, is the flow of air leaving the RPT device. Vent flow rate, Qv, is the flow of air leaving a vent to allow washout of exhaled gases. Leak flow rate, Ql, is the flow rate of unintentional leak from a patient interface system. Respiratory flow rate, Qr, is the flow of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. The pressure in the patient interface (mask pressure) is given the symbol Pm, while the treatment pressure, which represents a target value to be achieved by the mask pressure Pm at the current instant of time, is given the symbol Pt.

1.5.4 Terms for Ventilators

Adaptive Servo-Ventilator (ASV): A servo-ventilator that has a changeable rather than a fixed target ventilation. The changeable target ventilation may be learned from some characteristic of the patient, for example, a respiratory characteristic of the patient.

Backup rate: A parameter of a ventilator that establishes the respiratory rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template P(F) is zero-valued at the end of expiration, i.e., P(F)=0 when F=1, the EEP is equal to the EPAP.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Servo-assistance: Pressure support minus minimum pressure support.

Spontaneous Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the inspiratory portion of the breathing cycle by the patient's efforts.

Typical recent ventilation: The typical recent ventilation Vtyp is the value around which recent measures of ventilation over some predetermined timescale tend to cluster, that is, a measure of the central tendency of the measures of ventilation over recent history.

Ventilator: A mechanical device that provides pressure support to a patient to perform some or all of the work of breathing.

1.5.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx)

(the nasal part of the pharynx), the oropharynx (mesopharynx) (the oral part of the pharynx), and the laryngopharynx (hypopharynx).

OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A management system for managing a chronic condition of a user, the system comprising at least:
    a device configured for managing the chronic condition, including one or more processors, the device configured for communication with a first monitor configured to be wearable by the user and operative to generate a first signal associated with a first physiological parameter of the user, wherein the one or more processors of the device are configured to:
        access (1) a plurality of generated signals associated with a plurality of physiological parameters, the plurality of generated signals including the first signal; and (2) one or more environmental parameters comprising local airborne irritant data and/or local seasonal factor data;
        based on the accessed plurality of generated signals, derive the plurality of physiological parameters, the plurality of physiological parameters including the first physiological parameter;
        analyze the derived plurality of physiological parameters and the one or more environmental parameters, to detect a trigger pattern associated with one or more of the analyzed derived plurality of physiological parameters and the one or more environmental parameters, the trigger pattern being indicative of a probable event of exacerbation of the chronic condition;
        assess a predetermined activity based on a combination of the derived physiological parameters and the one or more environmental parameters; and
        control activation of an automated response based on the detection of the trigger pattern,
        wherein the automated response is a communication for warning that a user refrain from performing the predetermined activity based on the assessment of the predetermined activity, the predetermined activity being an activity that the user may want to perform, wherein the assessment of the predetermined activity includes determining, using statistical models, whether the predetermined activity poses a health risk to the user, and wherein whether the predetermined activity poses a health risk to the user depends on whether certain physiological and non-physiological combinations of parameters are met.

2. The system of claim 1, wherein the system further includes a monitor generating at least one of the plurality of generated signals.

3. The system of claim 1, wherein the device is further configured for receiving from a second monitor an additional generated physiological signal associated with an additional physiological parameter of the user, for an analysis, the second monitor being a stationary monitor.

4. The system of claim 3 wherein at least one of the first and the second monitor comprises one of a ballistocardiogram sensor, a heart rate monitor, a photoplethysmography sensor, a breathing monitor, an acoustic monitor including a sound sensor, a non-contact motion sensor, a monitor configured to detect motion by radio frequency transmission and reception, a galvanic skin response sensor, an activity sensor, a spirometer, a gas sensor, and a temperature sensor.

5. The system of claim 1 wherein the first signal associated with at least one parameter of the plurality of physiological parameters is generated by a non-contact motion sensing apparatus.

6. The system of claim 1 wherein said one or more processors is configured to determine a motion of the user from one of the plurality of physiological parameters, said motion being one of a movement of the user's chest due to respiration, a sway motion, a sway motion cancellation, rollover in bed, and falling out of bed.

7. The system of claim 1 wherein the plurality of physiological parameters includes detected physiological parameters from sensors positioned in different locations.

8. The system of claim 7 wherein the one or more processors of the device is configured to select, based on a location of the user, at least one of said sensors in different locations from which to receive a generated physiological parameter.

9. The system of claim 7 wherein the sensors in different locations comprise a first sensor located in a bedroom and a second sensor at a non-bedroom location.

10. The system of claim 1 wherein the device is portable and integrated with a portable alarm triggered by the automated response.

11. The system of claim 1 wherein the one or more processors are further configured to apply trend monitoring to determine the trigger pattern of the user indicative of a probable event of exacerbation of the chronic condition.

12. The system of claim 11 wherein the trend monitoring comprises evaluating data derived from people other than the user.

13. The system of claim 11 wherein the trend monitoring comprises determining a user-specific trigger based on manually entered feedback from the user.

14. The system of claim 1 wherein the one or more processors are configured to analyze the plurality of physiological parameters and the one or more environmental parameters with a supervised classification system.

15. The system of claim 1 wherein the one or more processors are configured to analyze the plurality of physiological parameters and the one or more environmental parameters by applying averaged decisions trees with random forests.

16. The system of claim 1 wherein the device is further configured to track a baseline threshold of at least one of the plurality of the physiological parameters.

17. The system of claim 1 wherein processor instructions of the one or more processors to analyze the plurality of physiological parameters and the one or more environmental parameters comprise rule thresholds that are varied based on adaptive probabilistic weightings from one or both of user specific and population based demographic data.

18. The system of claim 1 wherein a derived physiological parameter is one of breathing rate, heart rate, blood pressure, cough signature, wheeze, snore, sleep disordered breathing, Cheyne-Stokes Respiration, sleep condition, and electrodermal response.

19. The system of claim 1 wherein the one or more processors are configured to process any one or more of inspiration time, expiration time, a ratio of inspiration-to-expiration time, and respiratory waveform shape to detect the trigger pattern.

20. The system of claim 18 wherein said one or more processors are configured to evaluate a derived physiological parameter by applying detrended fluctuation analysis (DFA) to detect a change in the parameter over a period of time on an order of days, weeks, months or years.

21. The system of claim 20 wherein the derived physiological parameter is respiratory rate, and, the applying comprises processing of respiratory rate variability (RRV).

22. The system of claim 20 wherein the derived physiological parameter is heart rate, and wherein the applying comprises processing of heart rate variability (HRV).

23. The system of claim 22 wherein said one or more processors are configured to process both HRV data and galvanic skin response (GSR) data to generate an estimate of a balance between sympathetic and parasympathetic activation, wherein said balance is indicative of stability or progression of the chronic condition.

24. The system of claim 18 wherein a derived physiological parameter is a cough signature and wherein said one or more processors are configured to classify the cough signature based on at least one of: whether the cough occurs in a spasms, whether the cough is dry or productive; and whether it is persistent.

25. The system of claim 24 wherein said one or more processors are configured to identify one of asthma, gastroesophageal reflux disease, upper airway cough syndrome based on the classification of the cough signature.

26. The system of claim 24 wherein said one or more processors are configured to track a breathing pattern of the user based on combining data associated with the cough signature, and at least one of a breathing signal, heart rate data, blood pressure data, and motion sensor data.

27. The system of claim 24 wherein said one or more processors are configured to determine a sleep score based on detected coughing, and to estimate a change in risk of an exercise induced event causing the chronic condition to worsen for the user.

28. The system of claim 1 wherein the device is configured to track at least some of the physiological parameters during daytime and nighttime.

29. The system of claim 28 wherein a tracked physiological parameter is tracked by sensing an audio sound produced by the user during sleep.

30. The system of claim 29 wherein a tracked physiological parameter is determined in relation to its occurrence during a detected sleep stage including any one of light sleep, deep sleep and REM sleep.

31. The system of claim 1 wherein the plurality of physiological parameters and the one or more environmental parameters includes an environmental parameter based on at least one of climate data and geographic data.

32. The system of claim 1 wherein the device is configured to interface with a medical information system storing medical records of one or both of the user and other users, and wherein an analysis of the plurality of physiological parameters and the one or more environmental parameters comprises an analysis of a parameter based on data accessed from the medical records of one or both of the user and the other users.

33. The system of claim 1 wherein the one or more processors are configured to analyze received or accessed geographical data to determine whether there is a risk, or a change in risk, of exacerbation of the chronic condition.

34. The system of claim 1 wherein the automated response based on the detection of the trigger pattern comprises a communication for application of a treatment by using a treatment device adapted for treating the chronic condition of the user.

35. The system of claim 1 wherein the automated response based on the detection of the trigger pattern comprises a communication for instructing a user to effect a treatment of the chronic condition before performing a predetermined activity.

36. The system of claim 1 wherein the device comprises a smart-phone or smart-watch.

37. The system of claim 1 further comprising a smart-case or a cover, wherein the device is configured to detect a proximity of the smart-case or cover that houses or at least partially covers, or couples to, the device or one of the monitors.

38. The system of claim 36 wherein the device is configured to generate an alert when a smart case is not within a predefined range of the device.

39. The system of claim 1 wherein the one or more processors of the device is configured to determine a treatment, a medication dosage, a change of treatment or a change of a medication dosage based on the trigger pattern.

40. The system of claim 39 wherein the automated response comprises a communication for managing the treatment or medication dosage that is determined.

41. The system of claim 1 wherein the chronic condition is a chronic respiratory condition.

42. The system of claim 41, wherein the chronic condition managed is asthma, and wherein a determined treatment or medication dosage is one of: a number of puffs from an inhaler; and a quantity on a metered inhaler.

43. The system of claim 41 wherein the chronic condition is COPD, and wherein a determined treatment or medication dosage is a treatment from one of an inhaler, nebulizer, and supplemental oxygen tank.

44. The system of claim 40 wherein the trigger pattern indicative of a probable event of exacerbation of the chronic condition is indicative of an asthma condition and is based on any one or combination of breathing features and heart rate features, the breathing features including one or more of breathing rate, inspiration and expiration times and their ratio, breathing amplitude as assessed by local amplitude detection, comparison to personalised baseline measures related to breathing rate, and the heart rate features including one or more of heart rate variability and comparison to personalised baseline measures related to heart rate.

45. The system of claim 1 wherein the chronic condition is a chronic heart condition.

46. The system of claim 45 wherein the trigger pattern indicative of a probable event of exacerbation of the chronic condition is indicative of a congestive heart failure condition.

47. The system of claim 1 wherein the device includes an input interface for receiving the plurality of physiological parameters and the one or more environmental parameters, wherein the received parameters comprise any one or more of exercise data, breathing data, a cardiac data, a skin temperature data, skin coloration data, a sleep quality data, and blood pressure data, local weather data, and an indoor environmental data.

48. The system of claim 1 further comprising a respiratory pressure therapy device and a patient interface, the respiratory pressure therapy device configured to provide a respiratory treatment for the chronic condition via the patient interface.

49. The system of claim 1 wherein the device is further configured to receive subjective input of a user.

* * * * *